(12) United States Patent
Hauser et al.

(10) Patent No.: US 11,702,623 B2
(45) Date of Patent: Jul. 18, 2023

(54) DEVICE AND METHOD FOR MICROFLUIDICS-BASED 3D BIOPRINTING

(71) Applicant: KING ABDULLAH UNIVERSITY OF SCIENCE AND TECHNOLOGY, Thuwal (SA)

(72) Inventors: Charlotte A. E. Hauser, Thuwal (SA); Sakandar Rauf, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 628 days.

(21) Appl. No.: 16/612,580

(22) PCT Filed: Mar. 29, 2018

(86) PCT No.: PCT/IB2018/052189
§ 371 (c)(1),
(2) Date: Nov. 11, 2019

(87) PCT Pub. No.: WO2018/207037
PCT Pub. Date: Nov. 15, 2018

(65) Prior Publication Data
US 2020/0199514 A1 Jun. 25, 2020

Related U.S. Application Data

(60) Provisional application No. 62/504,959, filed on May 11, 2017.

(51) Int. Cl.
*C12M 1/26* (2006.01)
*B33Y 70/00* (2020.01)
(Continued)

(52) U.S. Cl.
CPC ........... *C12M 33/00* (2013.01); *A61L 27/227* (2013.01); *A61L 27/3886* (2013.01); *A61L 27/52* (2013.01); *B33Y 70/00* (2014.12); *B33Y 30/00* (2014.12)

(58) Field of Classification Search
None
See application file for complete search history.

(56) References Cited

U.S. PATENT DOCUMENTS

| | | | |
|---|---|---|---|
| 5,445,612 | A | 8/1995 | Terakura et al. |
| 8,729,032 | B2 | 5/2014 | Nagai et al. |

(Continued)

FOREIGN PATENT DOCUMENTS

| | | |
|---|---|---|
| CN | 105085622 A | 11/2015 |
| CN | 109224654 A | 1/2019 |

(Continued)

OTHER PUBLICATIONS

Hölzl et al., Biofabrication 8: 032002 (2016).*
(Continued)

*Primary Examiner* — Erin M. Bowers
(74) *Attorney, Agent, or Firm* — Ajay A. Jagtiani; Miles & Stockbridge P.C.

(57) ABSTRACT

The present invention relates to a device and a method for building a 3D object by mixing a bioink solution, a buffer solution capable of inducing gelation of the bioink solution and a dispersion containing micro and/or nanoparticles, and ejecting the formed hydrogel out of a nozzle. The present invention further relates to a method of obtaining a hydrogel.

8 Claims, 20 Drawing Sheets

(51) Int. Cl.
  *A61L 27/22* (2006.01)
  *A61L 27/38* (2006.01)
  *A61L 27/52* (2006.01)
  *B33Y 30/00* (2015.01)

(56) References Cited

U.S. PATENT DOCUMENTS

| | | | |
|---|---|---|---|
| 10,537,828 | B2 | 1/2020 | Baxter et al. |
| 2011/0113053 | A1 | 5/2011 | Khan et al. |
| 2013/0023460 | A1 | 1/2013 | Hauser et al. |
| 2014/0349933 | A1 | 11/2014 | Hauser et al. |
| 2015/0038428 | A1 | 2/2015 | Hauser et al. |
| 2016/0136895 | A1 | 5/2016 | Beyer et al. |
| 2016/0288414 | A1 | 10/2016 | Ozbolat et al. |
| 2016/0375177 | A1 | 12/2016 | Hauser et al. |
| 2017/0296760 | A1 | 10/2017 | Lee et al. |
| 2018/0030501 | A1 | 2/2018 | Bourdeau et al. |
| 2018/0361025 | A1 | 12/2018 | Lancaster et al. |
| 2019/0219572 | A1 | 7/2019 | Mehra et al. |
| 2019/0321291 | A1 | 10/2019 | Connolly et al. |
| 2020/0148720 | A1 | 5/2020 | Hauser et al. |
| 2020/0199514 | A1 | 6/2020 | Hauser et al. |
| 2020/0247046 | A1 | 8/2020 | Malaquin et al. |
| 2021/0114276 | A1 | 4/2021 | Nelson et al. |
| 2021/0121639 | A1 | 4/2021 | Miri Ramsheh et al. |

FOREIGN PATENT DOCUMENTS

| | | |
|---|---|---|
| CN | 111172100 A | 5/2020 |
| EP | 0 723 646 B1 | 7/1996 |
| JP | 2005-028216 A | 2/2005 |
| JP | 2013-009598 A | 1/2013 |
| JP | 2013009598 A | 1/2013 |
| JP | 2015-13850 A | 1/2015 |
| JP | 2016-79190 A | 5/2016 |
| JP | 2016-530874 A | 10/2016 |
| JP | 2017-501136 A | 1/2017 |
| JP | 2017501136 A | 1/2017 |
| JP | 2020-519605 A | 7/2020 |
| JP | 2002-320815 A | 11/2020 |
| KR | 10-1596014 B1 | 2/2016 |
| WO | 2014/104981 A1 | 7/2014 |
| WO | 2014/186581 A1 | 11/2014 |
| WO | 2014/197999 A1 | 12/2014 |
| WO | WO 2014/197999 * | 12/2014 |
| WO | 2015/066705 A1 | 5/2015 |
| WO | WO 2015/066705 * | 5/2015 |
| WO | 2015/080670 A9 | 6/2015 |
| WO | 2015/080671 A1 | 6/2015 |
| WO | 2016/123693 A1 | 8/2016 |
| WO | 2016/144259 A1 | 9/2016 |
| WO | 2017/089963 A1 | 6/2017 |
| WO | 2018/020737 A1 | 2/2018 |
| WO | 2018/207036 A1 | 11/2018 |
| WO | 2018/207037 A1 | 11/2018 |
| WO | 2020/162835 A1 | 8/2020 |

OTHER PUBLICATIONS

Lim et al., ACS Biomater. Sci. Eng. 2: 1752-1762 (2016).*
Hölz et al., ACS Sustainable Chem. Eng. 5: 828-834 (2017; published Oct. 25, 2016).*
International Search Report and Written Opinion received in PCT Application No. PCT/IB2021/057625 dated Dec. 14, 2021.
International Search Report and Written Opinion received in PCT Application No. PCT/IB2021/057624 dated Dec. 13, 2021.
International Search Report and Written Opinion received in PCT Application No. PCT/IB2021/057623 dated Dec. 13, 2021.
International Search Report and Written Opinion received in PCT Application No. PCT/IB2021/057996 dated Dec. 20, 2021.
International Search Report and Written Opinion received in PCT Application No. PCT/IB2021/057973 dated Dec. 20, 2021.
International Search Report and Written Opinion received in PCT Application No. PCT/IB2021/059652 dated Feb. 8, 2022.
Cembran et al., "Biomimetic Materials and Their Utility in Modeling the 3-Dimensional Neural Environment", iScience, vol. 23, pp. 1-16 (2020).
Cunha et al., "3D Culture of adult mouse neural stem cells within functionalized self-assembling peptide scaffolds", International Journal of Nanomedicine, vol. 6, pp. 943-955 (2011).
Marchini et al., "Multi-Functionalized Self-Assembling Peptides as Reproducible 3D Cell Culture Systems Enabling Differentiation and Survival of Various Human Neural Stem Cell Lines", frontiers in Neuroscience, vol. 14, Article 413, pp. 1-11 (2020).
Ranjan et al., "A microfiber scaffold-based 3D in vitro human neuronal culture model of Alzheimer's disease", The Royal Society of Chemistry, vol. 8, pp. 4861-4874 (2020).
Zhang et al., "Compatability of neural stem cells with functionalized self-assembling peptide scaffold in vitro", Biotechnology and Bioprocess Engineering, vol. 15, pp. 545-551 (2010).
Arab, "Novel Nanofibrous Peptide Scaffolds for Tissue Regeneration", PhD Thesis, Kind Abdullah University of Science and Technology, pp. 1-131 (2019).
Ikeno et al., "Effects of self-assembling peptide hydrogel scaffold on bone regeneration with recombinant human bone morphogenetic protein-2", The International Journal of Oral and Maxillofacial Implants, vol. 28, No. 5, pp. 283-289 (2013).
Liu et al., "Stiffness-mediated mesenchymal stem cell fate decision in 3D-bioprinted hydrogels", Burns and Trauma, vol. 8, pp. 1-13 (2020).
Sundararajan et al., "Use of cyanobacterial gas vesicles as oxygen carriers in cell culture", Cytotechnology, vol. 52, pp. 139-149 (2006).
Upadhyay et al., "Understanding Gas Vesicles and Its Scope in Biotechnological Applications", Advances in Biotechnology and Microbiology, vol. 11, Issue 2, pp. 1-13 (2018).
Gungor-Ozkerim, P. S.; Inci, I.; Zhang, Y. S.; Khademhosseini, A.; Dokmeci, M. R. Biomaterials Science 2018, 6, (5), 915-946.
Donderwinkel, I.; van Hest, J. C. M.; Cameron, N. R. Polymer Chemistry 2017, 8, (31), 4451-4471.
Gopinathan, J.; Noh, I. Biomater Res 2018, 22, 11-11.
Khademhosseini, A.; Camci-Unal, G., 3D Bioprinting in Regenerative Engineering:: Principles and Applications. CRC Press: 2018.
Gjorevski, N.; Sachs, N.; Manfrin, A.; Giger, S.; Bragina, M. E.; Ordonez-Moran, P.; Clevers, H.; Lutolf, M. P. Nature 2016, 539, (7630), 560-564.
Hauser, C. A. E.; Deng, R.; Mishra, A.; Loo, Y.; Khoe, U.; Zhuang, F.; Cheong, D. W.; Accardo, A.; Sullivan, M. B.; Riekel, C.; Ying, J. Y.; Hauser, U. A. Proceedings of the National Academy of Sciences 2011, 108, (4), 1361-1366.
Loo, Y.; Lakshmanan, A.; Ni, M.; Toh, L. L.; Wang, S.; Hauser, C. A. E. Nano Letters 2015, 15, (10), 6919-6925.
Seow, W. Y.; Salgado, G.; Lane, E. B.; Hauser, C. A. E. Scientific Reports 2016, 6, 32670.
Dhan, K. H.; Xue, B.; Robinson, R. C.; Hauser, C. A. E. Scientific Reports 2017, 7, (1), 12897.
Wang, H.; Ren, C.; Song, Z.; Wang, L.; Chen, X.; Yang, Z. Nanotechnology 2010, 21, (22), 225606.
Raeburn, J.; Pont, G.; Chen, L.; Cesbron, Y.; Lévy, R.; Adams, D. J. Soft Matter 2012, 8, (4), 1168-1174.
Betush, R. J.; Urban, J. M.; Nilsson, B. L. Peptide Science 2018, 110, (1), e23099.
Lakshmanan, A.; Cheong, D. W.; Accardo, A.; Di Fabrizio, E.; Riekel, C.; Hauser, C. A. Proc Natl Acad Sci U S A 2013, 110, (2), 519-24.
Bowerman, C. J.; Ryan, D. M.; Nissan, D. A.; Nilsson, B. L. Molecular BioSystems 2009, 5, (9), 1058-1069.
Senguen, F. T.; Lee, N. R.; Gu, X.; Ryan, D. M.; Doran, T. M.; Anderson, E. A.; Nilsson, B. L. Molecular BioSystems 2011, 7, (2), 486-496.
Surewicz, W. K.; Mantsch, H. H.; Chapman, D. Biochemistry 1993, 32, (2), 389-394.
Goormaghtigh, E.; Cabiaux, V.; Ruysschaert, J.-M. European Journal of Biochemistry 1990, 193, (2), 409-420.

(56) References Cited

OTHER PUBLICATIONS

Rivas-Arancibia, S.; Rodríguez-Martinez, E.; Badillo-Ramírez, I.; López-González, U.; Saniger, J. M. Frontiers in Molecular Neuroscience 2017, 10, (137).
Seow, W. Y.; Salgado, G.; Lane, E. B.; Hauser, C. A. E. Scientific Reports 2016, 6.
Tuncaboylu, D. C.; Argun, A.; Sahin, M.; Sari, M.; Okay, O. Polymer 2012, 53, (24), 5513-5522.
Murphy, S. V.; Atala, A. Nature Biotechnology 2014, 32, (8), 773-785.
Grinnell, F. Trends in cell biology 2003, 13, (5), 264-269.
Franco-Barraza, J.; Beacham, D. A; Amatangelo, M D.; Cukierman, E Current protocols in cell biology 2016, 71, (1), 10.9. 1-10.9.34.
Baker, B. M.; Chen, C. S. Journal of cell science 2012, 125, (13), 3015-3024.
Even-Ram, S.; Yamada, K. M. Current opinion in cell biology 2005, 17, (5), 524-532.
Lutolf, M. P.; Lauer-Fields, J. L.; Schmoekel, H. G.; Metters, A. T.; Weber, F. E.; Fields, G. B.; Hubbell, J. A. Proceedings of the National Academy of Sciences 2003, 100, (9), 5413-5418.
Mazzeo, M. S.; Chai, T.; Daviran, M.; Schultz, K. M. ACS applied bio materials 2018, 2, (1), 81-92.
Discher, D. E.; Mooney, D. J.; Zandstra, P. W. Science 2009, 324, (5935), 1673-1677.
Engler, A. J.; Sen, S.; Sweeney, H. L.; Discher, D. E. Cell 2006, 126, (4), 677-689.
Chaudhuri, O.; Gu, L.; Klumpers, D.; Darnell, M.; Bencherif, S. A.; Weaver, J. C.; Huebsch, N.; Lee, H.-p.; Lippens, E.; Duda, G. N. Nature materials 2016, 15, (3), 326-334.
Dalby, M. J.; Gadegaard, N.; Tare, R.; Andar, A.; Riehle, M. O.; Herzyk, P.; Wilkinson, C. D.; Oreffo, R. O. Nature materials 2007, 6, (12), 997-1003.
Haugh, M. G.; Vaughan, T. J.; Madl, C. M.; Raftery, R. M.; McNamara, L. M.; O'Brien, F. J.; Heilshorn, S. C. Biomaterials 2018, 171, 23-33.
Silbernagel, N.; Körner, A.; Balitzki, J.; Jaggy, M.; Bertels, S.; Richter, B.; Hippler, M.; Hellwig, A.; Hecker, M. Bastmeyer, M. Biomaterials 2020, 227, 119551.
Darnell, M.; Gu, L.; Mooney, D. Biomaterials 2018, 181, 182-188.
Kahin, K.; Khan, Z.; Albagami, M.; Usman, S.; Bahnshal, S.; Alwazani, H.; Majid, M.; Rauf, S.; Hauser, C. In Development of a robotic 3D bioprinting and microfluidic pumping system for tissue and organ engineering, Microfluidics, BioMEMS, and Medical Microsystems XVII, 2019; International Society for Optics and Photonics: p. 108750Q.
Mouser, V. H. M.; Melchels, F. P. W.; Visser, J.; Dhert, W. J. A.; Gawlitta, D.; Maida, J. Biofabrication 2016, 8, (3), 035003.
Chimene, D.; Peak, C. W.; Gentry, J. L.; Carrow, J. K.; Cross, L. M.; Mondragon, E.; Cardoso, G. B.; Kaunas, R. Gaharwar, A. K. ACS Applied Materials & Interfaces 2018, 10, (12), 9957-9968.
Bertassoni, L. E.; Cardoso, J. C.; Manoharan, V.; Cristino, A. L.; Bhise, N. S.; Araujo, W. A.; Zorlutuna, P.; Vrana, N. E.; Ghaemmaghami, A. M.; Dokmeci, M. R. Biofabrication 2014, 6, (2), 024105.
Markstedt, K.; Mantas, A.; Tournier, I.; Martíez Ávila, H. c.; Hagg, D.; Gatenholm, P. Biomacromolecules 2015, 16, (5), 1489-1496.
Bernal, P. N.; Delrot, P.; Loterie, D.; Li, Y.; Malda, J.; Moser, C.; Levato, R. Advanced materials 2019, 31, (42), 1904209.
Kang, H.-W.; Lee, S. J.; Ko, L K.; Kengla, C.; Yoo, J. J.; Atala, A. Nature biotechnology 2016, 34, (3), 312.
Hwang, T. L.; Shaka, A. J. Journal of Magnetic Resonance, Series A 1995, 112, (2), 275-279. 46. Derome, A. E.; Williamson, M. P. Journal of Magnetic Resonance (1969) 1990, 88, (1), 177-185.
Piotto, M.; Saudek, V.; Sklenář, V. Journal of Biomolecular NMR 1992, 2, (6), 661-665. 48. Sklenar, V.; Piotto, M.; Leppik, R.; Saudek, V. Journal of Magnetic Resonance, Series A 1993, 102, (2), 241-245.
Derome, A. E.; Williamson, M. P. Journal of Magnetic Resonance (1969) 1990, 88, (1), 177-185.
Micsonai, A.; Wien, F.; Kernya, L.; Lee, Y.-H.; Goto, Y.; Réfrégiers, M.; Kardos, J. Proceedings of the National Academy of Sciences 2015, 112, (24), E3095.
Maiti, N. C.; Apetri, M. M.; Zagorski, M. G.; Carey, P. R.; Anderson, V. E. Journal of the American Chemical Society 2004, 126, (8), 2399-2408.
Office Action received in Korean Application No. 10-2019-7036272 dated Oct. 21, 2022.
International Search Report and Written Opinion received in PCT Application No. PCT/IB2018/052173 dated Sep. 9, 2018.
International Search Report and Written Opinion received in PCT Application No. PCT/IB2018/052189 dated Aug. 28, 2018.
Office Action received in Saudi Arabian Application No. 519410522.
Office Action received in U.S. Appl. No. 16/612,881 dated Dec. 30, 2020.
Office Action received in U.S. Appl. No. 16/612,881 dated May 20, 2021.
Office Action received in Korean Application No. 10-2019-7036277 dated Sep. 29, 2021.
Office Action received in Saudi Arabian Application No. 519410521.
Loo et al., "Peptide Biolink: Self-Assembling Nanofibrous Scaffolds for Three-Dimensional Organotypic Cultures", Nano Letters, vol. 15, pp. 6919-6925 (2015).
Bowie et al., "Deciphering the Message in Protein Sequences: Tolerance of Amino Acid Substitutions", Science, vol. 247, pp. 1306-1310 (1990).
Burgess et al., "Possible Dissociation of the Heparin-binding Mitogenic Activities of Heparin-binding (Acid Fibroblast) Growth Factor-1 from Its Receptor-binding Activities by Site-directed Mutagenesis of a Single Lysine Residue", The Journal of Cell Biology, vol. 111, pp. 2129-2138 (1990).
Loo et al., "Peptide Bioink: Printable Nanofibrous Scaffolds for 3D Organotypic Cultures", vol. 15, XP055486589 (2015).
Fichman et al., "Self-assembly of short peptides to form hydrogels: Design of building blocks, physical properties and technological applications", Acta Biomaterials, vol. 10, pp. 1671-1682 (2014).
Loo, Y.; Chan, Y. S.; Szczerbinska, I.; Tan, B. C.; Wan, A. C.; Ng, H. H.; Hauser, C. A. A Chemically Well-Defined, Self-Assembling 3D Substrate for Long-Term Culture of Human Pluripotent Stem Cells. ACS Appl. Bio Mater. 2019, 2, 1406-1412.
Lee, J. H.; Jung, H. W.; Kang, I.-K.; Lee, H. B. Cell behaviour on polymer surfaces with different functional groups. Biomaterials 1994, 15, 705-711.
Guo, S.; Zhu, X.; Li, M.; Shi, L.; Ong, J. L. T.; Janćzewski.D.; Neoh, K. G. Parallel Control over Surface Charge and Wettability Using Polyelectrolyte Architecture: Effect on Protein Adsorption and Cell Adhesion. ACS Appl. Mater. Interfaces 2016, 8, 30552-30563.
Hauser, C. A. E.; Zhang, S. Designer self-assembling peptide nanofiber biological materials. Chem. Soc. Rev. 2010, 39, 2780-2790.
Bowerman, C. J.; Ryan, D. M.; Nissan, D. A.; Nilsson, B. L. The Effect of Increasing Hydrophobicity on the Self-Assembly of Amphipathic β-Sheet Peptides Mol. Biosyst. 2009, 5, 1058-1069.
Susapto, H. H.; Alhattab, D.; Abdelrahman, S.; Khan, Z.; Alshehri, S.; Kahin, K.; Ge, R.; Moretti, M.; Emwas, A. H.; Hauser, C. A. E. Ultrashort Peptide Bioinks Support Automated Printing of Large-Scale Constructs Assuring Long-Term Survival of Printed Tissue Constructs. Nano Lett. 2021, 2719.
Friedrichs, J.; Taubenberger, A.; Franz, C. M.; Muller, D. J. Cellular Remodelling of Individual Collagen Fibrils Visualized by Time-lapse AFM. J. Mol. Biol. 2007, 372, 594-607.
Nakayama, M.; Amano, M.; Katsumi, A.; Kaneko, T.; Kawabata, S.; Takefuji, M.; Kaibuchi, K. Rho-kinase and myosin II activities are required for cell type and environment specific migration. Genes Cells 2005, 10, 107-117.
Beadle, C.; Assanah, M. C.; Monzo, P.; Vallee, R.; Rosenfeld, S. S.; Canoil, P. The Role of Myosin II in Glioma Invasion of the Brain. Mol. Biol. Cell 2008, 19, 3357-3368.
Friedl, P.; Wolf, K.; Lammerding, J. Nuclear mechanics during cell migration. Curr. Opin. Cell Biol. 2011, 23, 55-64.

(56) References Cited

OTHER PUBLICATIONS

Balzer, E. M.; Tong, Z.; Paul, C. D.; Hung, W.-C.; Stroka, K. M.; Boggs, A. E.; Martin, S. S.; Konstantopoulos, K. Physical confinement alters tumor cell adhesion and migration phenotypes FASEB J. 2012, 26, 4045-4056.

Khatau, S. B.; Bloom, R. J.; Bajpai, S.; Razafsky, D.; Zang, S.; Giri, A.; Wu, P.-H.; Marchand, J.; Celedon, A.; Hale, C. M.; Sun, S. X.; Hodzic, D.; Wirtz, D. The distinct roles of the nucleus and nucleus-cytoskeleton connections in three-dimensional cell migration. Sci. Rep. 2012, 2, No. 488.

Wen, J. H.; Vincent, L. G.; Fuhrmann, A.; Choi, Y. S.; Hribar, K. C.; Taylor-Weiner, H.; Chen, S.; Engler, A. J. Interplay of matrix stiffness and protein tethering in stem cell differentiation. Nat. Mater. 2014, 13, 979-987.

Thievessen, I.; Thompson, P. M.; Berlemont, S.; Plevock, K. M.; Plotnikov, S. V.; Zemljic-Harpf, A.; Ross, R. S.; Davidson, M. W.; Danuser, G.; Campbell, S. L.; Waterman, C. M. Vinculin-actin interaction couples actin retrograde flow to focal adhesions, but is dispensable for focal adhesion growth. J. Cell Biol. 2013, 202, 163-177.

Humphries, J. D.; Wang, P.; Streuli, C.; Geiger, B.; Humphries, M. J.; Ballestrem, C. Vinculin controls focal adhesion formation by direct interactions with talin and actin. J. Cell. Biol. 2007, 179, 1043-1057.

Ode, A.; Schoon, J.; Kurtz, A.; Gaetjen, M.; Ode, J. E.; Geissler, S.; Duda, G. N. CD73/5'-ecto-nucleotidase acts as a regulatory factor in osteo-/chondrogenic differentiation of mechanically stimulated mesenchymal stromal cells. Eur. Cells Mater. 2013, 25, 37-47.

Aslan, H.; Zilberman, Y.; Kandel, L.; Liebergall, M.; Oskouian, R. J.; Gazit, D.; Gazit, Z. Osteogenic differentiation of noncultured immunoisolated bone marrow-derived CD105+ cells. Stem Cells 2006, 24, 1728-1737.

Huang, S.; Ingber, D. E. The structural and mechanical complexity of cell-growth control. Nat. Cell Biol. 1999, 1, No. E131.

McBeath, R.; Pirone, D. M.; Nelson, C. M.; Bhadriraju, K.; Chen, C. S. Cell shape, cytoskeletal tension, and RhoA regulate stem cell lineage commitment. Dev. Cell 2004, 6, 483-495.

Katz, B.-Z.; Zamir, E.; Bershadsky, A.; Kam, Z.; Yamada, K. M.; Geiger, B. Physical state of the extracellular matrix regulates the structure and molecular composition of cell-matrix adhesions. Mol. Biol. Cell 2000, 11, 1047-1060.

Cukierman, E.; Pankov, R.; Stevens, D. R.; Yamada, K. M. Taking cell-matrix adhesions to the third dimension. Science 2001, 294, 1708-1712.

Fischbach, C.; Kong, H. J.; Hsiong, S. X.; Evangelista, M.B.; Yuen, W.; Mooney, D. J. Cancer cell angiogenic capability is regulated by 3D culture and integrin engagement. Proc. Natl. Acad Sci. U S A 2009, 106, 399-404.

Hsiong, S. X.; Boontheekul, T.; Huebsch, N.; Mooney, D. J. Cyclic arginine-glycine-aspartate peptides enhance three-dimensional stem cell osteogenic differentiation. Tissue Eng., Part A 2009, 15, 263-272.

Park, J. S.; Huang, N. F.; Kurpinski, K. T.; Patel, S.; Hsu, S.; Li, S. Mechanobiology of mesenchymal stem cells and their use in cardiovascular repair. Front. Biosci. 2007, 12, 5098-5116.

Tan, S.; Fang, J. Y.; Yang, Z.; Nimni, M. E.; Han, B. The synergetic effect of hydrogel stiffness and growth factor on osteogenic differentiation Biomaterials 2014, 35, 5294-5306.

Knight, B.; Laukaitis, C.; Akhtar, N.; Hotchin, N. A.; Edlund, M.; Horwitz, A. R. Visualizing muscle cell migration in situ. Curr. Biol. 2000, 10, 576-585.

Roskelley, C.; Desprez, P.; Bissell, M. Extracellular matrix- dependent tissue-specific gene expression in mammary epithelial cells requires both physical and biochemical signal transduction. Proc. Natl. Acad. Sci. U.S.A. 1994, 91, 12378-12382.

Thievessen, I; Fakhri, N.; Steinwachs, J.; Kraus, V.; McIsaac, R. S.; Gao, L.; Chen, B.-C.; Baird, M. A.; Davidson, M. W.; Betzig, E.; et al. Vinculin is required for cell polarization, migration, and extracellular matrix remodeling in 3D collagen. FASEB J. 2015, 29, 4555-4567.

Case, L. B.; Baird, M. A.; Shtengel, G.; Campbell, S. L.; Hess, H. F.; Davidson, M. W.; Waterman, C. M. Molecular mechanism of vinculin activation and nanoscale spatial organization in focal adhesions. Nat. Cell Biol. 2015, 17, 880-892.

Carisey, A.; Ballestrem, C. Vinculin, an adapter protein in control of cell adhesion signalling. Eur. J. Cell Biol. 2011, 90, 157-163.

Xu, W.; Baribault, H.; Adamson, E. D. Vinculin knockout results in heart and brain defects during embryonic development. Development 1998, 125, 327-337.

Kumar, G.; Tison, C. K.; Chatteijee, K.; Pine, P. S.; McDaniel, J. H.; Salit, M. L.; Young, M. F.; Simon, C. G., Jr. The determination of stem cell fate by 3D scaffold structures through the control of cell shape. Biomaterials 2011, 32, 9188-9196.

Pablo Rodríguez, J.; González, M.; Ríos, S.; Cambiazo, V. Cytoskeletal organization of human mesenchymal stem cells (MSC) changes during their osteogenic differentiation J. Cell. Biochem. 2004, 93, 721-731.

Treiser, M. D.; Yang, E. H.; Gordonov, S.; Cohen, D. M.; Androulakis, I. P.; Kohn, J.; Chen, C. S.; Moghe, P. V. Cytoskeleton- based forecasting of stem cell lineage fates. Proc. Natl. Acad. Sci. U S A 2010, 107, 610-615.

Hunter, G. K.; Hauschka, P. V.; Poole, R. A.; Rosenberg, L. C.; Goldberg, H. A. Nucleation and inhibition of hydroxyapatite formation by mineralized tissue proteins. Biochem. J. 1996, 317, 59-64.

Wang, J.; Cui, X.; Zhou, Y.; Xiang, Q. Core-shell PLGA/ collagen nanofibers loaded with recombinant FN/CDHs as bone tissue engineering scaffolds. Connect Tissue Res. 2014, 55, 292-298.

Khan, S. N.; Lane, J. M. Bone Tissue Engineering: Basic Science and Clinical Concepts. Orthopedic Tissue Engineering; CRC Press, 2004; pp. 177-194.

Oreffo, R. O.; Kusec, V.; Romberg, S.; Triffitt, J. T. Human bone marrow osteoprogenitors express estrogen receptor-alpha and bone morphogenetic proteins 2 and 4 mRNA during osteoblastic differentiation. J. Cell. Biochem. 1999, 75, 382-392.

Frank, O.; Heim, M.; Jakob, M.; Barbera, A.; Schafer, D.; Bendik, I.; Dick, W.; Heberer, M.; Martin, I. Real-time quantitative RT-PCR analysis of human bone marrow stromal cells during osteogenic differentiation in vitro. J. Cell. Biochem. 2002, 85, 737-746.

Miron, R.; Zhang, Y. Osteoinduction: a review of old concepts with new standards. J. Dent. Res. 2012, 91, 736-744.

Rittling, S. R.; Matsumoto, H. N.; Mckee, M. D.; Nanci, A.; An, X. R.; Novick, K. E.; Kowalski, A. J.; Noda, M.; Denhardt, D. T. Mice lacking osteopontin show normal development and bone structure but display altered osteoclast formation in vitro. J. Bone Miner. Res. 1998, 13, 1101-1111.

Chellaiah, M. A.; Kizer, N.; Biswas, R.; Alvarez, U.; Strauss-Schoenberger, J.; Rifas, L.; Rittling, S. R.; Denhardt, D. T.; Hruska, K. A. Osteopontin deficiency produces osteoclast dysfunction due to reduced CD44 surface expression. Mol. Biol. Cell 2003, 14, 173-189.

Bax, D. V.; Rodgers, U. R.; Bilek, M. M.; Weiss, A. S. Cell adhesion to tropoelastin is mediated via the C-terminal GRKRK motif and integrin $\alpha V\beta 3$. J. Biol. Chem. 2009, 284, 28616-28623.

Taddese, S.; Weiss, A. S.; Jahreis, G.; Neubert, R. H.; Schmelzer, C. E. In vitro degradation of human tropoelastin by MMP-12 and the generation of matrikines from domain 24. Matrix Biol. 2009, 28, 84-91.

Getie, M.; Schmelzer, C.; Neubert, R. Characterization of peptides resulting from digestion of human skin elastin with elastase. Proteins 2005, 61, 649-657.

Phillips, J. E.; Petrie, T. A.; Creighton, F. P.; García, A. J. Human mesenchymal stem cell differentiation on self-assembledmonolayers presenting different surface chemistries. Acta Biomater. 2010, 6, 12-20.

Nemir, S.; West, J. L. Synthetic materials in the study of cell response to substrate rigidity. Ann. Biomed. Eng. 2010, 38, 2-20.

Holst, J.; Watson, S.; Lord, M. S.; Eamegdool, S. S.; Bax, D. V.; Nivison-Smith, L. B.; Kondyurin, A.; Ma, L.; Oberhauser, A. F.; Weiss, A. S.; Rasko, J. E. J. Substrate elasticity provides mechanical signals for the expansion of hemopoietic stem and progenitor cells. Nat. Biotechnol. 2010, 28, 1123.

(56) References Cited

OTHER PUBLICATIONS

Rowlands, A. S.; George, P. A.; Cooper-White, J. J. Directing osteogenic and myogenic differentiation of MSCs: interplay of stiffness and adhesive ligand presentation. Am. J. Physiol.: Cell Physiol. 2008, 295, C1037-C1044.
Saha, K.; Keung, A. J.; Irwin, E. F.; Li, Y.; Little, L.; Schaffer, D. V.; Healy, K. E. Substrate modulus directs neural stem cell behavior. Biophys. J. 2008, 95, 4426-4438.
Examination Report received in European Application No. 18 720 665.1 dated Oct. 25, 2022.
Official Action received in Japanese Application No. 2019-561747 dated Sep. 13, 2022.
Examination Report received in Saudi Arabian Application No. 521430991 dated Aug. 18, 2022.
Office Action received in U.S. Appl. No. 16/612,580 dated Sep. 21, 2022.
Office Action received in U.S. Appl. No. 17/401,800 dated Aug. 30, 2022.
International Search Report and Written Opinion received in International Application No. PCT/IB2022/055194 dated Sep. 20, 2022.
International Search Report and Written Opinion received in International Application No. PCT/IB2022/055054 dated Sep. 26, 2022.
Alshehri et al., "Scaffolds from Self-Assembling Tetrapeptides Support 3D Spreading, Osteogenic Differentiation, and Angiogenesis of Mesenchymal Stem Cells", Biomacromolecules, vol. 22, pp. 2094-2106 (2021).
Chen et al., "Hydrogelation of the Short Self-Assembling Peptide I3QGK Regulated by Transglutaminase and Use for Rapid Hemostasis", ACS Appl Matter Interfaces, vol. 28, pp. 17833-17841 (2016).
Echalier et al., "Modular bioink for 3D printing of biocompatible hydrogels: sol-gel polymerization of hybrid peptides anti polymers", RSC Advances, vol. 7, pp. 12231-12235 (2017).
Holzl et al., "Bioink properties before, during and after 3D printing", Biofabrication, vol. 8, 032002 (2016).
Holz et al., "High-Power 365 nm UV LED Mercury Arc Lamp Replacement for Photochemistry and Chemical Photolithography", ACS Sustainable Chemistry & Engineering, vol. 5, pp. 828-834 (2017).
Lim et al., "New Visible-Light Photoinitiating System for Improved Print Fidelity in Gelatin-Based Bioinks", ACS Biomaterials Science and Engineering, vol. 2, pp. 1752-1762 (2016).
Loo et al., "Bioprinting synthetic self-assembling peptide hydrogels for boimedical applications", Biomedical Materials, vol. 11, No. 1 (2015).
Sekine et al., "Capillary Networks for Bio-Artificial Three-Dimensional Tissues Fabricated Using Cell Sheet Based Tissue Engineering", International Journal of Molecular Sciences, vol. 22, No. 92, pp. 1-12 (2021).
Susapto et al., "Ultrashort Peptide Bioinks Support Automated Printing of Large-Scale Constructs Assuring Long-Term Survival of Printed Tissue Constructs", Nano Letters, vol. 21, pp. 2719-2729 (2021).
Yan et al., "Advances in portable electrospinning devices for in situ delivery of personalized wound care", Nanoscale, vol. 11, pp. 19166-19178 (2019).
Notice of Allowance received in corresponding Korean Application No. 10-2019-7036277 dated Apr. 6, 2022.
Office Action received in Japanese Patent Application No. 2019-561848 dated Apr. 5, 2022.
Office Action received in Japanese Patent Application No. 2019-561747 dated Mar. 15, 2022.
Notice of Allowance received in Korean Application No. 10-2019-7036377 dated Apr. 6, 2022.
Search Report and Written Opinion received in PCT Application No. PCT/IB2021/060795.
Ali et al., "A Non-Canonical NRPS Is Involved in the Synthesis of Fungisporin and Related Hydrophobic Cyclic Tetrapeptides in Penicillium chrysogenum", Plos One, vol. 9, Issue 6, pp. 1-10 (2014).
Alrashoudi et al., "Fabrication of a Lateral Flow Assay for Rapid In-Field Detection of COVID-19 Antibodies Using Additive Manufacturing Printing Technologies", International Journal of Bioprinting, vol. 7, Issue 4, pp. 76-84 (2021).
Farrera-Soler et al., "Identification of immunodominant linear epitodes from SARS-CoV-2 patient plasma", Plos One, pp. 1-15 (2020).
Saatci, Newly developed methods for SARS-CoV-2 detection [SARS-CoV-2 saptanmasinda yeni gelistririlen tani yontemleri], Turk J. Biochem., 45 (5), pp. 465-474 (2020).
Vasco et al., "Macrocyclization of Peptide Side Chains by the Ugi Reaction: Achieving Peptide Folding and Exocyclic N-Functionalization in One Shot", Journal of Organic Chemistry, 80, pp. 6697-6707 (2015).
Xiang et al., "A novel double antibody sandwich-lateral flow immunoassay for the rapid and simple detection of hepatitis C virus", International Journal of Molecular Medicine, 30, pp. 1041-1047 (2012).
Examination Report received in European Patent Application No. 18 718 922.0 dated May 20, 2022.
Office Action received in U.S. Appl. No. 17/401,800 dated Apr. 11, 2022.
Huebsch, N.; Arany, P. R.; Mao, A. S.; Shvartsman, D.; Ali, O. A.; Bencherif, S. A.; Rivera-Feliciano, J.; Mooney, D. J. Harnessing traction-mediated manipulation of the cell/matrix interface to control stem-cell fate. Nat. Mater. 2010, 9, 518.
Kabiri, K.; Omidian, H.; Hashemi, S.; Zohuriaan-Mehr, M. Synthesis of fast-swelling superabsorbent hydrogels: effect of crosslinker type and concentration on porosity and absorption rate. Eur. Polym. J. 2003, 39, 1341-1348.
Hale, B. W.; Goodrich, L. R.; Frisbie, D. D.; McIlwraith, C. W.; Kisiday, J. D. Effect of scaffold dilution on migration of mesenchymal stem cells from fibrin hydrogels. Am. J. Vet. Res. 2012, 73, 313-318.
Cuchiara, M. P.; Allen, A. C.; Chen, T. M.; Miller, J. S.; West, J. L. Multilayer microfluidic PEGDA hydrogels. Biomaterials 2010, 31, 5491-5497.
Cheng, R.; Yan, Y.; Liu, H.; Chen, H.; Pan, G.; Deng, L.; Cui, W. Mechanically enhanced lipo-hydrogel with controlled release of multi-type drugs for bone regeneration. Appl. Mater. Today 2018, 12, 294-308.
Engler, A. J.; Sen, S.; Sweeney, H. L.; Discher, D. E. Matrix elasticity directs stem cell lineage specification. Cell 2006, 126, 677-689.
Sivaraj, K. K.; Adams, R. H. Blood vessel formation and function in bone. Development 2016, 143, 2706-2715.
Kim, S.; Cha, C. Enhanced mechanical and electrical properties of heteroscaled hydrogels infused with aqueous-dispersible hybrid nanofibers. Biofabrication 2020, 12, No. 015020.
Hwang, T. L.; Shaka, A. J., Water Suppression That Works. Excitation Sculpting Using Arbitrary Wave-Forms and Pulsed-Field Gradients. J. Magn. Reson. 1995, 112, (2), 275-279.
Derome, A. E.; Williamson, M. P., Rapid-Pulsing Artifacts in Double-Quantum-Filtered COSY. J. Magn. Reson. 1990, 88, (1), 177-185.
Piotto, M.; Saudek, V.; Sklenář, V., Gradient-Tailored Excitation for Single-Quantum NMR Spectroscopy of Aqueous Solutions. J. Biomol. NMR 1992, 2, (6), 661-665.
Gilbert, D. F.; Erdmann, G.; Zhang, X.; Fritzsche, A.; Demir, K.; Jaedicke, A.; Muehlenberg, K.; Wanker, E. E.; Boutros, M., A novel multiplex cell viability assay for high- throughput RNAi screening. PloS One 2011, 6, (12), e28338.
Arab, "Novel Nanofibrous Peptide Scaffolds for Tissue Regeneration", Dissertation, King Abdullah University of Science and Technology, Thuwal, Saudi Arabia, Apr. 2019.
Ikeno et al., "Effects of self-assembling peptide hydrogel scaffold on bone regeneration with recombinant human bone morphogenetic protein-2"; The International Journal of Oral and Maxillofacial Implants; vol. 28, No. 5, pp. e283-289 (2013).
Liu et al., "Stiffness-mediated mesenchymal stem cell fate decision in 3D-bioprinted hydrogels"; Burns & Trauma, vol. 8, pp. 1-13 (2020).
International Search Report and Written Opinion received in International Application No. PCT/IB2021/057623 dated Dec. 13, 2021.
Examination Report received in Saudi Arabian Application No. 519410522 dated Aug. 2, 2022.

(56) References Cited

OTHER PUBLICATIONS

Search Report and Written Opinion received in PCT Application No. PCT/IB2022/051913 dated Jun. 14, 2022.
Office Action received in U.S. Appl. No. 16/612,580 dated Jun. 6, 2022.
Bowie et al., "Deciphering the Message in Protein Sequences: Tolderance to Amino Acid Substitutions", Science, vol. 249, pp. 1306-1310 (1990).
Burgess et al., "Possible dissociation of the heparin-binding and mitogenic activities of heparin-binding (acidic fibroblast) growth factor-1 from its receptor-binding activities by site-directed mutagenesis of a single lysine residue", J. cell Biol, vol. 111, pp. 2129-2138 (1990).
Loo et al., "Peptide Bioink: Self-Assembling Nanofibrous Scaffolds for Three-Dimensional Organotypic Cultures", vol. 15, pp. 1-13, XP055486589 (2015).
Substantive Examination Report received in Saudi Arabian Application No. 519410521 dated Aug. 31, 2021.
Li, Z.; Huang, S.; Liu, Y.; Yao, B.; Hu, T.; Shi, H.; Xie, J.; Fu, X. Scientific Reports 2018, 8, (1), 8020.
Jorgensen, W. L.; Tirado-Rives, J. Proceedings of the National Academy of Sciences of the United States of America 2005, 102, (19), 6665.
Dodda, L. S.; Cabeza de Vaca, I.; Tirado-Rives, J.; Jorgensen, W. L. Nucleic Acids Research 2017, 45, (W1), W331-W336.
Abraham, M. J.; Murtola, T.; Schulz, R.; Páll, S.; Smith, J. C.; Hess, B.; Lindahl, E. SoftwareX 2015, 1-2, 19-25.
Darden, T.; York, D.; Pedersen, L. The Journal of Chemical Physics 1993, 98, (12), 10089-10092.
Berendsen, H. J. C.; Postma, J. P. M.; Gunsteren, W. F. v.; DiNola, A.; Haak, J. R. The Journal of Chemical Physics 1984, 81, (8), 3684-3690.
Bussi, G.; Donadio, D.; Parrinello, M. The Journal of Chemical Physics 2007, 126, (1), 014101.
Kim, Y. H.; Baek, N. S.; Han, Y. H.; Chung, M.-A.; Jung, S.-D. Journal of neuroscience methods 2011, 202, (1), 38-44.
Riss, T. L.; Valley, M. P.; Zimprich, C. A.; Niles, A. L.; Kupcho, K. R.; Lazar, D. F. 60. Howe, B.; Umrigar, A.; Tsien, F. JoVE (Journal of Visualized Experiments) 2014, (83), e50203.
Howe, B.; Umrigar, A.; Tsien, F. JoVE (Journal of Visualized Experiments) 2014, (83), e50203.
Perrier, A. L.; Tabar, V.; Barberi, T.; Rubio, M. E.; Bruses, J.; Topf, N.; Harrison, N. L.; Studer, L. Proceedings of the National Academy of Sciences 2004, 101, (34), 12543-12548.
Kang, J.; Lee, I. Cardiovascular Pathology 2006, 15, (4), 218-221.
Blakely, B. D.; Bye, C. R.; Fernando, C. V.; Horne, M. K.; Macheda, M. L.; Stacker, S. A.; Arenas, E.; Parish, C. L. PloS one 2011, 6, (3), e18373.
Bowie et al., "Deciphering the Message in Protein Sequences: Tolerance to Amino Acid Substitutions", Science, vol. 47, pp. 1306-1310 (1990).
Burgess et al., "Possible Dissociation of the Heparin-binding Mitogenic Activities of Haparin-binding (Acidic Fibroblast) Growth Factor-1 from Its Receptor-binding Activities by Site-directed Mutagenesis of a Single Lysine Residue", The Journal of Cell Biology, vol. 111, pp. 2129-2138 (1990).
Loo et al, "Peptide Bioink: Printable Nanofibrous Scaffolds for 3D Organotyic Cultures", vol. 15, XP055486589 (2015).
Suspato et al, "Ultrashort Peptide Bioinks Support Automated Printing of Large-Scale Constructs Assuring Long-Term Survival of Printed Tissue Constructs", Nano Lett. 21, 7, pp. 2719-2729 (2021).
International Search Report and Written Opinion received in PCT Application No. PCT/IB2021/057622 dated Dec. 16, 2021.
Substantive Examination Report received in Saudi Arabian Application No. 519410522.
Fichman et al., "Self-assembly of short peptides to form hydrogels: Design of building blocks, physical properties and technological applications", Acta Biomaterialia, 16, pp. 1571-1582 (2014).
Gauthaman, K.; Venugopal, J. R.; Yee, F. C.; Biswas, A.; Ramakrishna, S.; Bongso, A. Osteogenic differentiation of human Wharton's jelly stem cells on nanofibrous substrates in vitro. Tissue Eng., Part A 2011, 17, 71-81.
Leng, Q.; Chen, L.; Lv, Y. RNA-based scaffolds for bone regeneration: application and mechanisms of mRNA, miRNA and siRNA. Theranostics 2020, 10, 3190.
Erdem, A.; Darabi, M. A.; Nasiri, R.; Sangabathuni, S.; Ertas, Y. N.; Alem, H.; Hosseini, V.; Shamloo, A.; Nasr, A. S.; Ahadian, S. 3D Bioprinting of Oxygenated Cell-Laden Gelatin Methacryloyl Constructs. Adv. Healthcare Mater. 2020, 9, No. 1901794.
Myeroff, C.; Archdeacon, M. Autogenous bone graft: donor sites and techniques. J. Bone Jt. Surg. 2011, 93, 2227-2236.
Silbernagel, N.; Körner, A.; Balitzki, J.; Jaggy, M.; Bertels, S.; Richter, B.; Hippler, M.; Hellwig, A.; Hecker, M. Bastmeyer, M.; Ullrich, N. D. Shaping the Heart: Structural and Functional Maturation of iPSC-Cardiomyocytes in 3D-Micro-Scaffolds. Bio- materials 2020, 227, No. 119551.
Silber, J. S.; Anderson, D. G.; Daffner, S. D.; Brislin, B. T.; Leland, J. M.; Hilibrand, A. S.; Vaccaro, A. R.; Albert, T. J. Donor site morbidity after anterior iliac crest bone harvest for single-level anterior cervical discectomy and fusion. Spine 2003, 28, 134-139.
Alonzo, M.; Alvarez Primo, F.; Anil Kumar, S.; Mudloff, J. A.; Dominguez, E.; Fregoso, G.; Ortiz, N.; Weiss, W. M. Joddar, B. Bone tissue engineering techniques, advances, and scaffolds for treatment of bone defects. Curr. Opin. Biomed. Eng. 2021, 17, No. 100248.
Pittenger, M. F.; Mackay, A. M.; Beck, S. C.; Jaiswal, R. K.; Douglas, R.; Mosca, J. D.; Moorman, M. A.; Simonetti, D. W.; Craig, S.; Marshak, D. R. Multilineage potential of adult human mesenchymal stem cells. Science 1999, 284, 143-147.
Pittenger, M. F.; Mackay, A. M.; Beck, S. C.; Jaiswal, R. K.; Douglas, R.; Mosca, J. D.; Moorman, M. A.; Simonetti, D. N.; Craig, S.; Marshak, D. R. Multilineage potential of adult human mesenchymal stem cells. Science 1999, 284, 143-147.
Ma, K.; Laco, F.; Ramakrishna, S.; Liao, S.; Chan, C. K. Differentiation of bone marrow-derived mesenchymal stem cells into multi-layered epidermis-like cells in 3D organotypic coculture Biomaterials 2009, 30, 3251-3258.
Petite, H.; Viateau, V.; Bensaid, W.; Meunier, A.; de Pollak, C.; Bourguignon, M.; Oudina, K.; Sedel, L.; Guillemin, G. Tissue-engineered bone regeneration. Nat. Biotechnol. 2000, 18, 959.
Takamine, Y.; Tsuchiya, H.; Kitakoji, T.; Kurita, K.; Ono, Y.; Ohshima, Y.; Kitoh, H.; Ishiguro, N.; Iwata, H. Distraction osteogenesis enhanced by osteoblastlike cells and collagen gel. Clin. Orthop. Relat. Res. 2002, 399, 240-246.
Kofidis, T.; Lebl, D. R.; Martinez, E. C.; Hoyt, G.; Tanaka, M.; Robbins, R. C. Novel injectable bioartilicial tissue facilitates targeted, less invasive, large-scale tissue restoration on the beating heart after myocardial injury. Circulation 2005, 112, I-173-I-177.
Yildirim, Y.; Naito, H.; Didié, M.; Karikkineth, B. C.; Biermann, D.; Eschenhagen, T.; Zimmermann, W.-H. Development of a biological ventricular assist device: preliminary data from a small animal model. Circulation 2007, 116, I-16-I-23.
Radisic, M.; Park, H.; Shing, H.; Consi, T.; Schoen, F. J.; Langer, R.; Freed, L. E.; Vunjak-Novakovic, G. Functional assembly of engineered myocardium by electrical stimulation of cardiac myocytes cultured on scaffolds. Proc. Natl. Acad. Sci. U.S.A. 2004, 101, 18129-18134.
Spadaccio, C.; Chachques, E.; Chello, M.; Covino, E.; Chachques, J. C.; Genovese, J. Predifferentiated adult stem cells and matrices for cardiac cell therapy. Asian Cardiovasc. Thorac. Ann. 2010, 18, 79-87.
Kutschka, I.; Chen, I. Y.; Kofidis, T.; Arai, T.; Von Degenfeld, G.; Sheikh, A. Y.; Hendry, S. L.; Pearl, J.; Hoyt, G.; Sista, R.; et al. Collagen matrices enhance survival of transplanted cardiomyoblasts and contribute to functional improvement of ischemic rat hearts. Circulation 2006, 114, I-167-I-173.
Orkin, R.; Gehron, P.; Mcgoodwin, E. B.; Martin, G.; Valentine, T.; Swarm, R. A murine tumor producing a matrix of basement membrane. J. Exp. Med. 1977, 145, 204-220.
Sethi, T.; Rintoul, R. C.; Moore, S. M.; MacKinnon, A. C.; Salter, D.; Choo, C.; Chilvers, E. R.; Dransfield, I.; Donnelly, S. C.;

(56) References Cited

OTHER PUBLICATIONS

Strieter, R.; et al. Extracellular matrix proteins protect small cell lung cancer cells against apoptosis: a mechanism for small cell lung cancer growth and drug resistance in vivo. Nat. Med. 1999, 5, 662-668.
Grant, D.; Kibbey, M.; Kinsella, J.; Cid, M.; Kleinman, H. The role of basement membrane in angiogenesis and tumor growth. Pathol., Res. Pract. 1994, 190, 854-863.
Fushimi, H.; Hiratsuka, T.; Okamura, A.; Ono, Y.; Ogura, I.; Nishimura, I. Recombinant collagen polypeptide as a versatile bone graft biomaterial. Commun. Mater. 2020, 1, No. 1.
Kang, P. L.; Huang, H. H.; Chen, T.; Ju, K. C.; Kuo, S. M. Angiogenesis-promoting effect of LIPUS on hADSCs and HUVECs cultured on collagen/hyaluronan scaffolds. Mater. Sci. Eng., C 2019, 102, 22-33.
Blokhuis, T.; Arts, J. C. Bioactive and osteoinductive bone graft substitutes: definitions, facts and myths. Injury 2011, 42, S26-S29.
Barradas, A.; Yuan, H.; van Blitterswijk, C. A.; Habibovic, P. Osteoinductive biomaterials: current knowledge of properties, experimental models and biological mechanisms. Eur. Cells Mater. 2011, 21, 407-429.
Habibovic, P.; de Groot, K. Osteoinductive biomaterials焙 properties and relevance in bone repair. J. Tissue Eng. Regener. Med. 2007, 1, 25-32.
Ramier, J.; Grande, D.; Bouderlique, T.; Stoilova, O.; Manolova, N.; Rashkov, I.; Langlois, V.; Albanese, P.; Renard, E. From design of bio-based biocomposite electrospun scaffolds to osteogenic differentiation of human mesenchymal stromal cells. J. Mater. Sci. Mater. Med. 2014, 25, 1563-1575.
Adler-Abramovich, L.; Gazit, E. The physical properties of supramolecular peptide assemblies: from building block association to technological applications Chem. Soc. Rev. 2014, 43, 6881-6893.
Biesalski, M. A.; Knaebel, A.; Tu, R.; Tirrell, M. Cell adhesion on a polymerized peptide-amphiphile monolayer. Biomaterials 2006, 27, 1259-1269.
Mata, A.; Hsu, L.; Capita, R.; Aparicio, C.; Henrikson, K.; Stupp, S. I. Micropatterning of bioactive self-assembling gels. Soft Matter 2009, 5, 1228-1236.
Eren, E. D.; Tansik, G.; Tekinay, A. B.; Guler, M. O. Mineralized peptide nanofiber gels for enhanced osteogenic differentiation. ChemNanoMat 2018, 4, 837-845.
Mata, A.; Geng, Y.; Henrikson, K. J.; Aparicio, C.; Stock, S. R.; Satcher, R. L.; Stupp, S. I. Bone regeneration mediated by biomimetic mineralization of a nanofiber matrix. Biomaterials 2010, 31, 6004-6012.
Derkus, B.; Okesola, B. O.; Barrett, D. W.; D'Este, M.; Chowdhury, T. T.; Eglin, D.; Mata, A. Multicomponent hydrogels for the formation of vascularized bone-like constructs in vitro. Acta Biomater. 2020, 109, 82-94.
Ghosh, M.; Halperin-Sternfeld, M.; Grigoriants, I.; Lee, J.; Nam, K. T.; Adler-Abramovich, L. Arginine-presenting peptide hydrogels decorated with hydroxyapatite as biomimetic scaffolds for bone regeneration. Biomacromolecules 2017, 18, 3541-3550.
Tsutsumi, H.; Kawamura, M.; Mihara, H. Osteoblastic differentiation on hydrogels fabricated from Ca2+-responsive self- assembling peptides functionalized with bioactive peptides. Bioorg Med. Chem. 2018, 26, 3126-3132.
Zhang, R.; Liu, Y.; Qi, Y.; Zhao, Y.; Nie, G.; Wang, X.; Zheng, S. Self-assembled peptide hydrogel scaffolds with VEGF and BMP-2 Enhanced in vitro angiogenesis and osteogenesis. Oral Dis. 2021, DOI: 10.1111/odi.13785, in press.
Misawa, H.; Kobayashi, N.; Soto-Gutierrez, A.; Chen, Y.; Yoshida, A.; Rivas-Carrillo, J. D.; Navarro-Alvarez, N. Tanaka, K.; Miki, A.; Takei, J.; et al. PuraMatrix facilitates bone regeneration in bone defects of calvaria in mice. Cell Transplant. 2006, 15, 903-910.

Ikeno, M.; Hibi, H.; Kinoshita, K.; Hattori, H.; Ueda, M. Effects of self-assembling peptide hydrogel scaffold on bone regeneration with recombinant human bone morphogenetic protein-2. Int. J. Oral Maxillofac. Implants 2013, 28, e283-9.
He, B.; Ou, Y.; Chen, S.; Zhao, W.; Zhou, A.; Zhao, J.; Li, H.; Jiang, D.; Zhu, Y. Designer bFGF-incorporated d-form self-assembly peptide nanofiber scaffolds to promote bone repair. Mater. Sci. Eng., C 2017, 74, 451-458.
Tsukamoto, J.; Naruse, K.; Nagai, Y.; Kan, S.; Nakamura, N.; Hata, M.; Omi, M.; Hayashi, T.; Kawai, T.; Matsubara, T. Efficacy of a self-assembling peptide hydrogel, SPG-178-gel, for bone regeneration and three-dimensional osteogenic nduction of dental pulp stem cells. Tissue Eng., Part A 2017, 23, 1394-1402.
Sun, Y.; Li, W.; Wu, X.; Zhang, N.; Zhang, Y.; Ouyang, S.; Song, X.; Fang, X.; Seeram, R.; Xue, W.; He, L.; Wu, W. Functional Self-Assembling Peptide Nanofiber Hydrogels Designed for Nerve Degeneration. ACS Appl. Mater. Interfaces 2016, 8, 2348-2359.
Guo, J.; Su, H.; Zeng, Y.; Liang, Y.-X.; Wong, W. M.; Ellis- Behnke, R. G.; So, K.-F.; Wu, W. Reknitting the injured spinal cord by self-assembling peptide nanofiber scaffold Nanomedicine 2007, 3, 311-321.
Liu, X.; Wang, X.; Wang, X.; Ren, H.; He, J.; Qiao, L.; Cui, F.-Z. Functionalized self-assembling peptide nanofiber hydrogels mimic stem cell niche to control human adipose stem cell behavior in vitro. Acta Biomater. 2013, 9, 6798-6805.
Rauf, S.; Susapto, H. H.; Kahin, K.; Alshehri, S.; Abdelrahman, S.; Lam, J. H.; Asad, S.; Jadhav, S.; Sundaramurthi, D.; Gao, X.; Hauser, C. A. E. Self-assembling tetrameric peptides allow in situ 3D bioprinting under physiological conditions. J. Mater. Chem. B 2021, 9, 1069-1081.
Susapto, H. H.; Alhattab, D.; Abdelrahman, S.; Khan, Z.; Alshehri, S.; Kahin, K.; Ge, R.; Moretti, M.; Emwas, A.-H. Hauser, C. A. E. Ultrashort Peptide Bioinks Support Automated Printing of Large-Scale Constructs Assuring Long-Term Survival of Printed Tissue Constructs. Nano Lett. 2021, 21, 2719-2729.
Arthur, A.; Zannettino, A.; Gronthos, S. The therapeutic applications of multipotential mesenchymal/stromal stem cells in skeletal tissue repair. J. Cell. Physiol. 2009, 218, 237-245.
Polo-Corrales, L.; Latorre-Esteves, M.; Ramirez-Vick, J. E. Scaffold design for bone regeneration. J. Nanosci. Nanotechnol. 2014, 14, 15-56.
Holmes, T. C. Novel peptide-based biomaterial scaffolds for tissue engineering. Trends Biotechnol. 2002, 20, 16-21.
Hauser, C. A.; Deng, R.; Mishra, A.; Loo, Y.; Khoe, U.; Zhuang, F.; Cheong, D. W.; Accardo, A.; Sullivan, M. B.; Riekel, C.; Ying, J. Y.; Hauser, U. A. Natural tri- to hexapeptides self-assemble in water to amyloid beta-type fiber aggregates by unexpected alpha-helical intermediate structures. Proc. Natl. Acad. Sci. U.S.A. 2011, 108, 1361-1366.
Lei, Y.; Gojgini, S.; Lam, J.; Segura, T. The spreading, migration and proliferation of mouse mesenchymal stem cells cultured inside hyaluronic acid hydrogels. Biomaterials 2011, 32, 39-47.
Sklenar, V.; Piotto, M.; Leppik, R.; Saudek, V. Journal of Magnetic Resonance, Series A 1993, 102, (2), 241-245.
Wilson, S. A.; Cross, L. M.; Peak, C. W.; Gaharwar, A. K. ACS applied materials & interfaces 2017, 9, (50), 43449-43458.
Final Office Action received in Japanese Application No. 2019-561884 dated Oct. 11, 2022.
Seliktar, D. Science 2012, 336, (6085), 1124-1128.
Williams, R. W.; Dunker, A. K. Journal of Molecular Biology 1981, 152, (4), 783-813.
Worton, R. G.; Duff, C., [27] Karyotyping. In Methods in enzymology, Elsevier: 1979; vol. 58, pp. 322-344.
Bharadwaz et al., "Recent trends in the application of widely used natural and synthetic polymer nanocomposites in bone tissue regeneration", Materials Science and Engineering C 110 110698 (2020).

\* cited by examiner

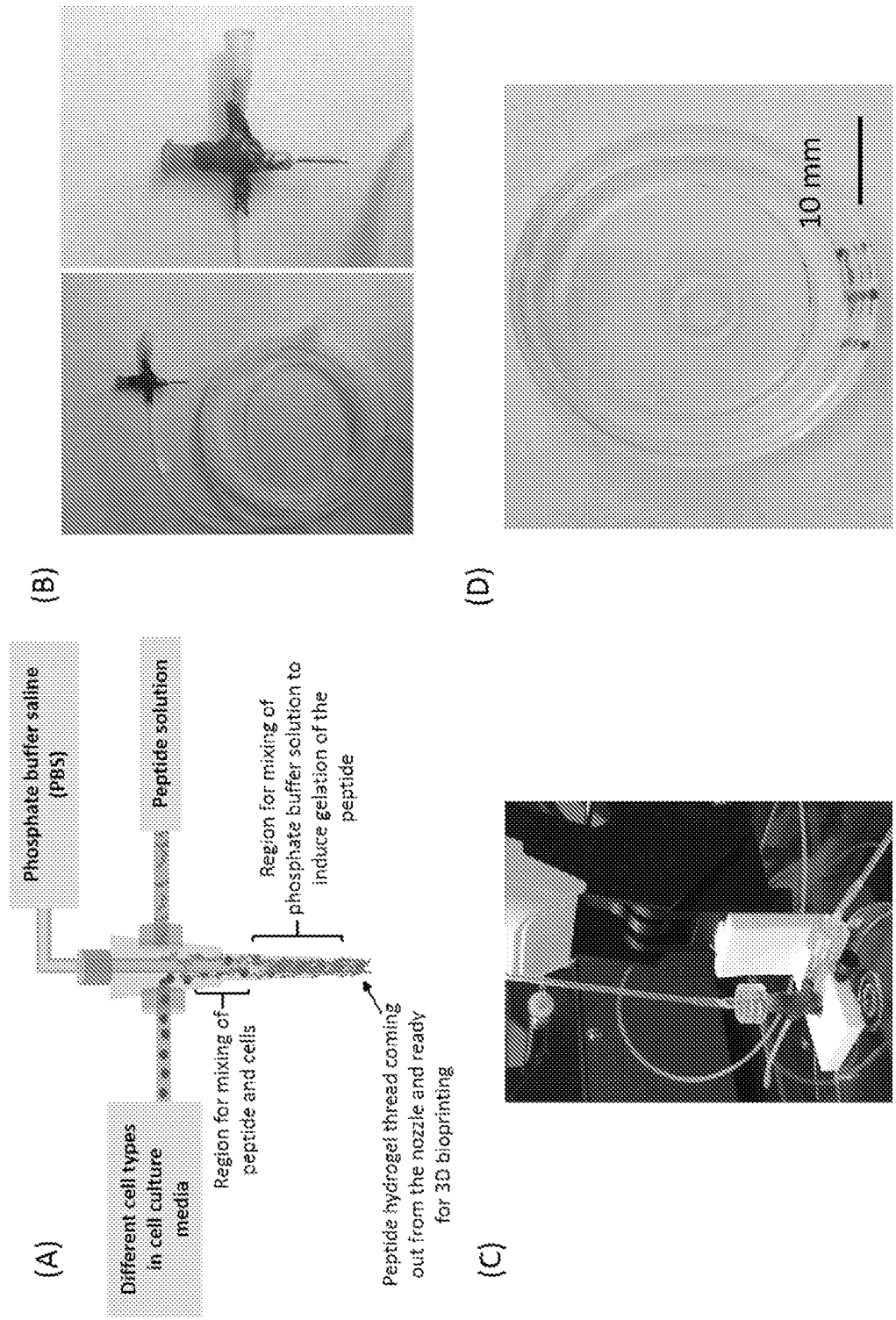
Figure 1 A - D

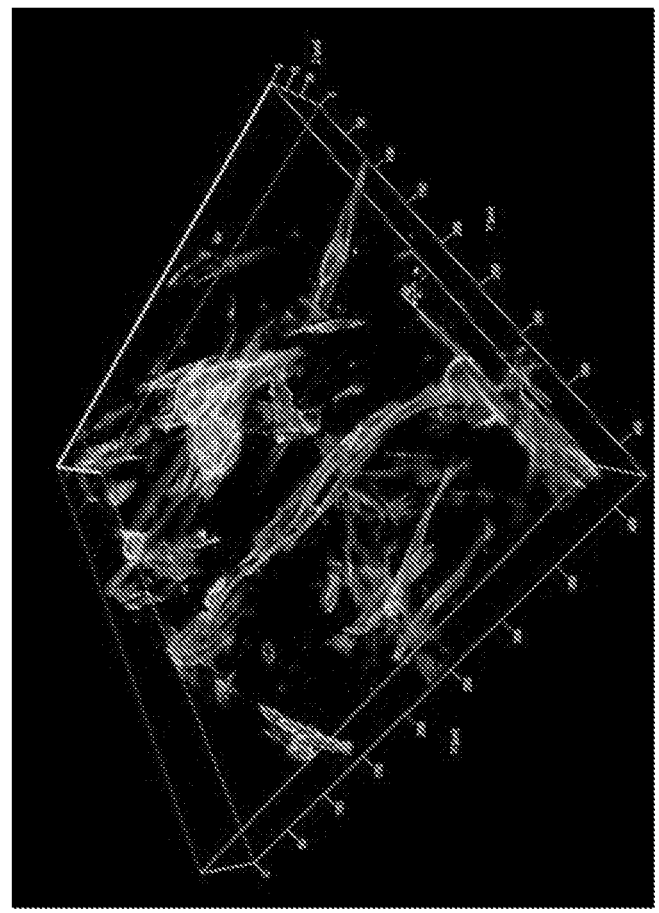
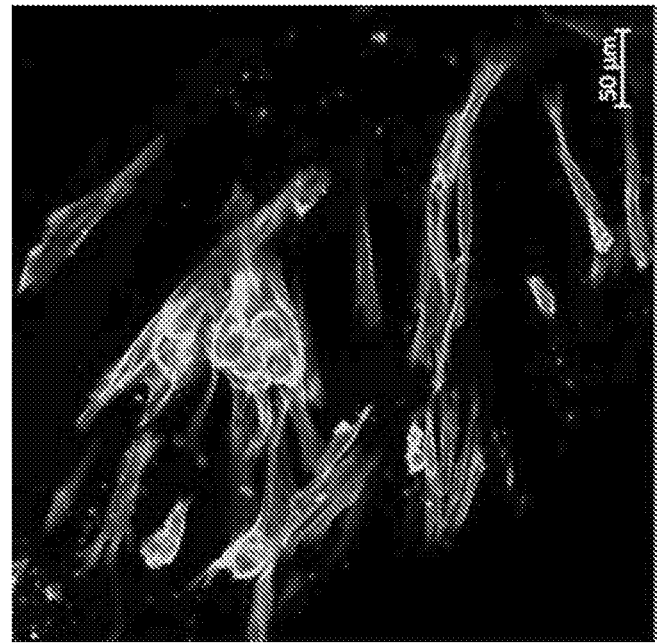
Figure 6

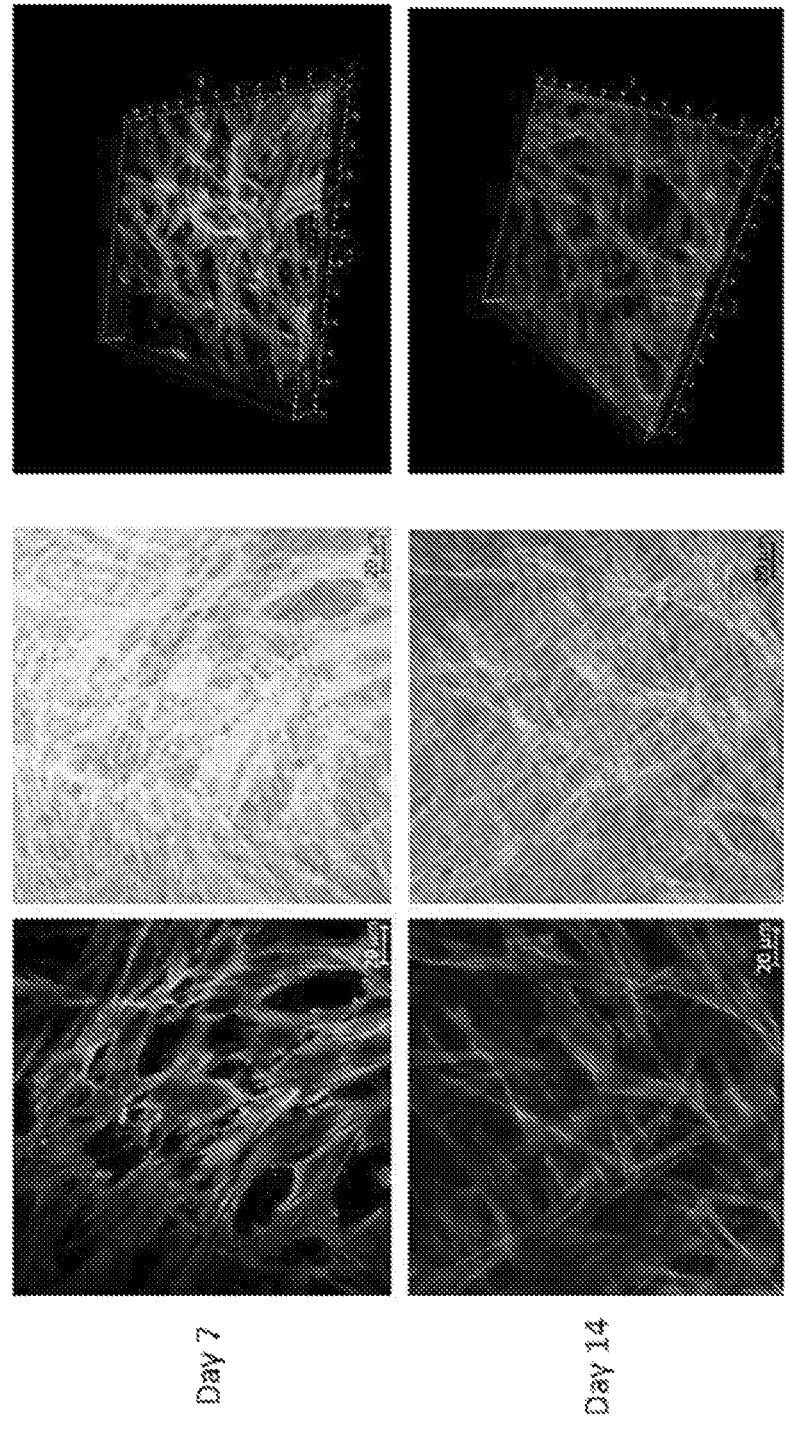
Figure 9 - continued

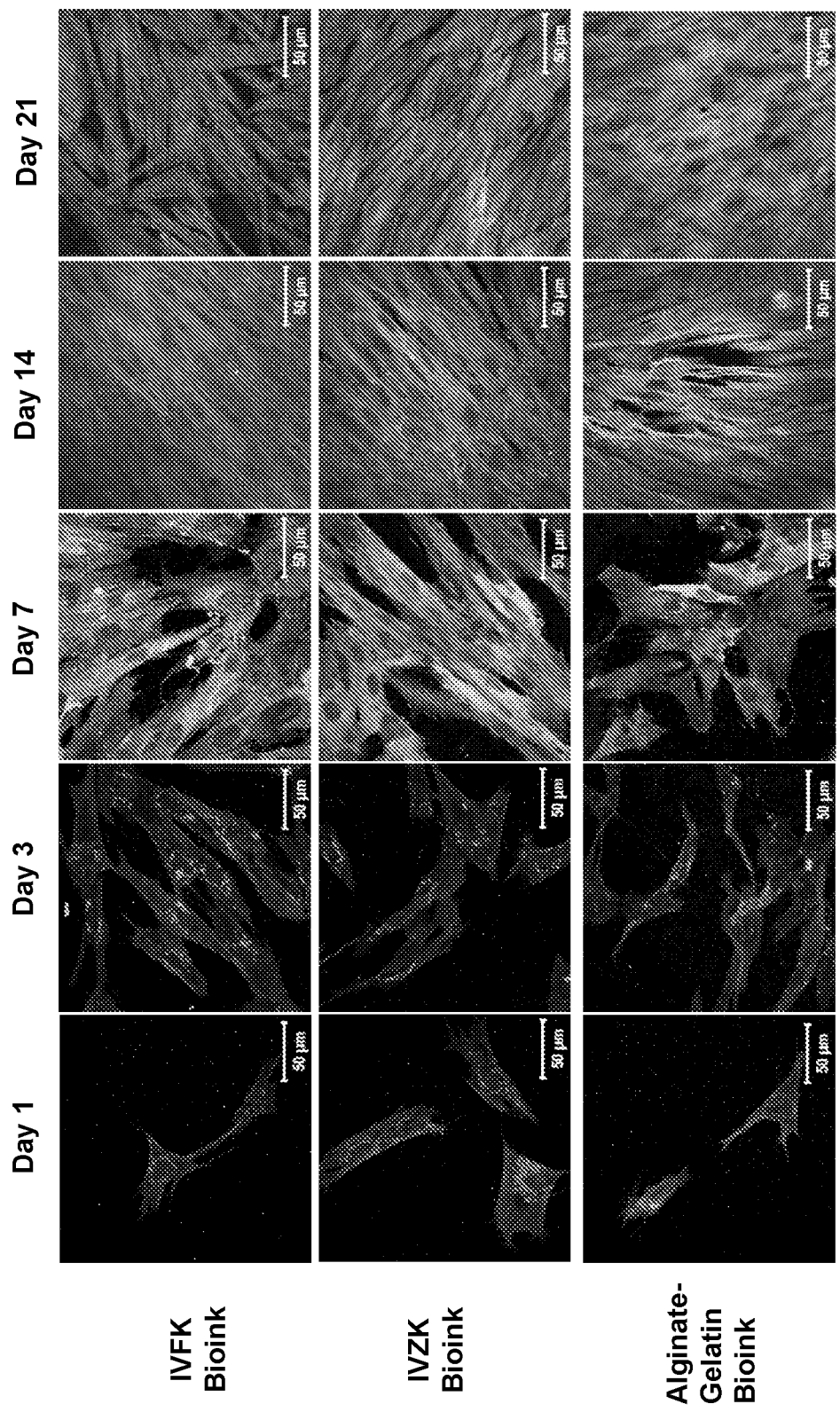

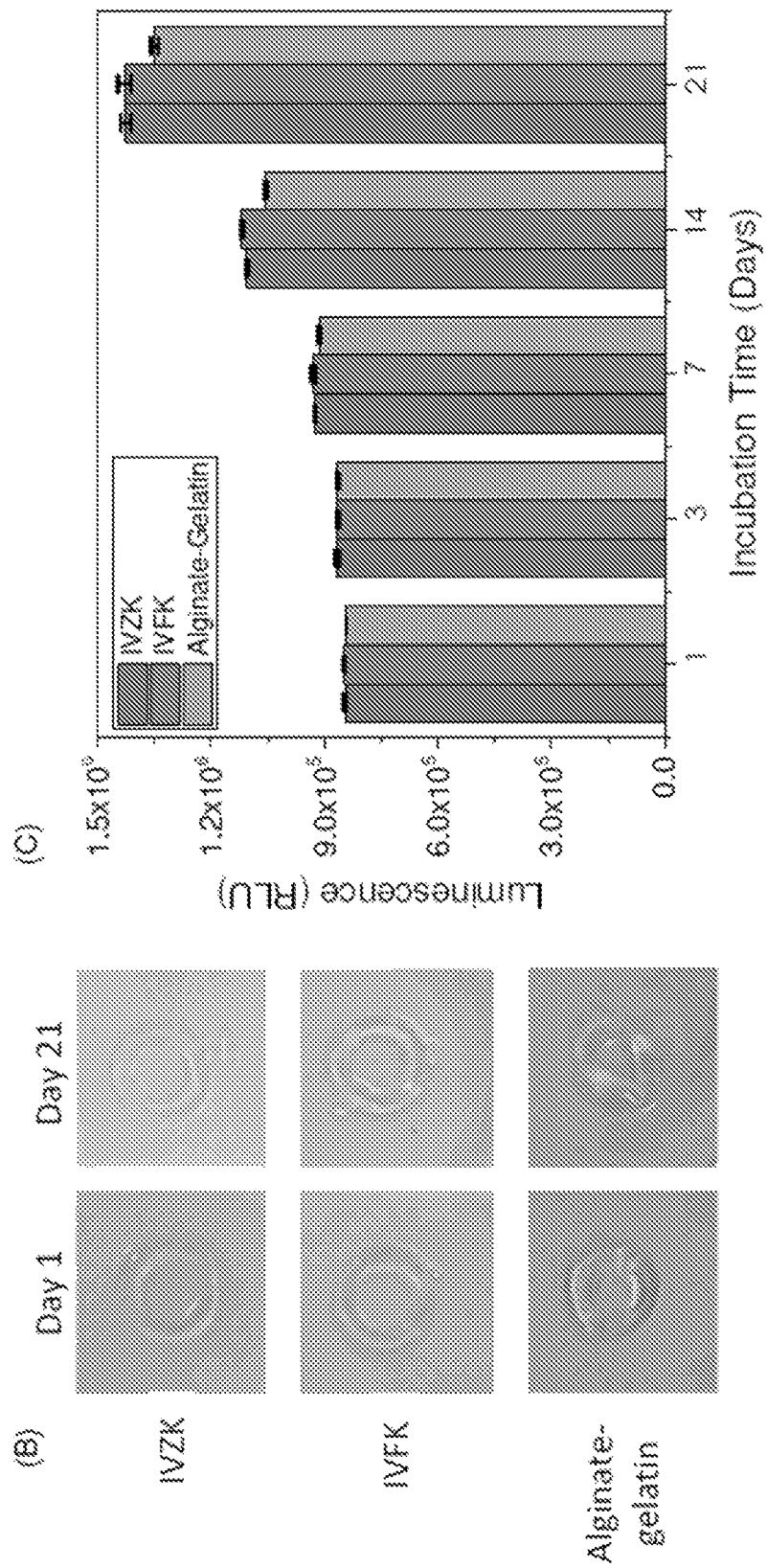
Figure 11 B and C

DEVICE AND METHOD FOR MICROFLUIDICS-BASED 3D BIOPRINTING

CROSS REFERENCE TO RELATED APPLICATIONS

This application is a National Stage Application of International Application Number PCT/IB2018/052189, filed Mar. 29, 2018; which claims priority to U.S. Provisional Application Ser. No. 62/504,959, filed May 11, 2017.

TECHNICAL FIELD

The present invention relates to a device and a method for building a 3D object. The present invention further relates to a method of obtaining a hydrogel.

BACKGROUND 3D printing technologies can be applied to build tissue-like structures, e.g. in the field of medicine and tissue engineering. Generally, these methods are referred to as 3D bioprinting. Typically, printing inks are used that are synthetic, e.g. polymers, or natural. Also materials from plants such as alginate can be used. In particular with natural materials there can be significant batch-to-batch variations, which has an impact on reproducibility and sustainability of the bio-printed 3D structures.

In 3D bioprinting usually a pre-polymer viscous solution is used to print in 3D, and after printing, either an initiator or (UV or visible) light is used for the polymerization of the 3D construct. Several factors are important for bioinks to be suitable for 3D bioprinting. These include biocompatibility, biomimetic structure, biodegradability, porosity and mechanical strength.

Despite recent advances in 3D bioprinting, there is still a need for improved devices and methods for printing of 3D objects.

SUMMARY OF THE INVENTION

The objective of the present invention is to provide a device and a method for building a 3D object, wherein the device for building a 3D object and the method for building a 3D object overcome one or more of the problems of the prior art.

A first aspect of the invention provides a device for building a 3D object from a representation of the object stored in a memory, the device comprising:
  a first inlet configured to take in a bioink solution, in particular a peptide solution,
  a second inlet configured to take in a buffer solution capable of inducing gelation of the bioink solution, preferably instantaneous gelation of the bioink solution,
  a third inlet configured to take in a dispersion,
  a fluid duct for mixing the bioink solution, the buffer solution and the dispersion to obtain a hydrogel, in particular a peptide hydrogel, and
  a nozzle configured to eject a hydrogel, in particular a peptide hydrogel to build the 3D object.

The device can comprise a 3D arm which guides the nozzle to build the 3D object with the desired three-dimensional structure. The memory storing the representation of the object can be part of the device. In other embodiments, the memory is external to the device.

Preferably, the device comprises two or more arms which can move in three dimensions and comprise at least two or three axes. The incorporation of multiple robotic arms allows for simultaneously printing different materials and thus can reduce overall print time.

In embodiments, the first inlet can be connected to a tank with the bioink solution and/or the second inlet can be connected to a tank with the buffer solution. The buffer solution can be in particular a phosphate buffer solution.

Bioink refers to a material that mimics an extracellular matrix environment. The bioink can be suitable to support the adhesion, proliferation, and differentiation of mammalian cells. The bioink can have the ability to be deposited as filament during an additive manufacturing process, e.g. 3D printing.

The bioink solution can be a peptide solution wherein the peptides are made from synthetic, but natural amino acid sequences. Such bioinks can closely resemble body like materials, thus avoiding immunological problems and potential inflammatory processes.

The fluid duct can be a microfluidic channel. In particular, the fluid duct can have a diameter of less than 1000 μm, preferably less than 200 μm.

The device of the first aspect can be used with peptide-based bioinks and offers a unique and novel combination for 3D bioprinting. The advantage of peptide-based bioinks is that these are synthetic amino acid sequences and closely resemble body-like materials. In particular, a synthetic, but naturally occurring and cost-effective peptide bioink can be provided with superior physical and chemical properties enabling instantaneous gelation.

The representation of the object can comprise information about a mixture level between the bioink solution and the buffer solution. For example, the representation can comprise information that in a first region of the object, a 2:1 ratio between bioink solution and buffer solution should be used and in a second region a 1:1 ratio between bioink solution and buffer solution should be used.

The representation can also comprise information about which pressure or flow rate should be used to eject the peptide hydrogel.

The device of the first aspect can be used to fabricate 3D tissue scaffolds or structures at the physiological milieu of choice, with suitable pH, ionic composition, and molarity, thus protecting the native cell function, which gives an advantage over existing printing devices that use chemical initiators or photo-polymerization (UV or visible light treatment).

The peptide bioinks also allow the printing of different materials (e.g. peptide micro or nanoparticles, gold or silver nanoparticles, nanowires, graphene, carbon nanotubes and quantum dots, for example) in 3D structures that can perform various functions. For example, the built structures can be used for imaging, sensing, catalysis and tuning of the mechanical properties of the peptide hydrogel. The versatility of printing the nanomaterials is demonstrated by printing the quantum dots and by the in-situ synthesis of silver nanoparticles in the 3D printed structures.

The device of the first aspect can have applications in materials science and in the field of biomedical engineering such as regenerative medicine, tissue engineering, wound healing (printing at the wound site), tissues and organs printing, prosthetics, medical implants, in vitro models and 3D tissue models for drug testing and biosensing.

The device of the first aspect can also be used directly in the surgical room during surgery to provide patients in need immediately with the printed tissue construct. A platform based on the device of the first aspect can also include a 3D image reconstruction system which enables the printing devices to take the image of an object and print it according to the user specifications.

Preferably, the nozzle comprises the fluid duct. Preferably, the fluid duct is arranged within the nozzle. For example, the fluid duct can be arranged along an axis of the nozzle. The fluid duct can be arranged such that it ends inside of the nozzle.

In a first implementation of the device for printing a 3D object according to the first aspect, the fluid duct comprises a first region for mixing the bioink solution and the dispersion to obtain a bioink-dispersion mixture and a second region for mixing the bioink-dispersion mixture with the buffer solution.

In a second implementation of the device for printing a 3D object according to the first aspect, the dispersion comprises a cell culture media. The cell culture media can for example comprise primary human skin fibroblast cells.

Preferably, the cell culture media comprises a plurality of cell types. In other embodiments, the cell culture media comprises only one type of cell types.

In a third implementation of the device for printing a 3D object according to the first aspect, the dispersion comprises micro and/or nanoparticles, preferably peptide microparticles, peptide nanoparticles, silver nanoparticles, gold nanoparticles, nanowires, quantum dots and/or carbon nanotubes.

The peptide micro or nanoparticles loaded with different drugs can be used for controlled drug delivery in the 3D printed structure. The advantage of using other types of nanoparticle such as silver nanoparticles, gold nanoparticles, nanowires, quantum dots and carbon nanotubes is that these nanoparticles can add imaging, sensing and catalysis abilities to the 3D printed peptide hydrogel structure.

In a fourth implementation of the device for printing a 3D object according to the first aspect, a plurality of cell types are encapsulated in the peptide microparticles and/or immobilized on the peptide microparticles, in particular on the peptide microparticle surface.

The advantage of encapsulating the plurality of cells in the peptide microbeads and subsequent 3D printing with the peptide hydrogel allow the precise positioning of different cell types in the 3D construct. This will allow an increase in vascularization of the 3D printed construct which is a requirement for the 3D bioprinted constructs.

In a further implementation of the device for printing a 3D object according to the first aspect, the device further comprises a heating module configured to heat the microfluidic fluid duct.

The heating module can comprise a coil with windings that are wrapped around the nozzle or a heating jacket. The heating module can be configured to heat the fluid duct to more than 60° C., preferably more than 80° C.

In a further implementation of the device according to the first aspect, the device further comprises a micromixer. Said micromixer can be used to enhance mixing of the peptide/bioink solution and cells to get a more homogeneous distribution of the cells across the 3D bioprinted construct. Said micromixer can be located in the fluid duct, in particular in said first region for mixing the bioink solution and the cell/dispersion to obtain a bioink-dispersion mixture.

The device can also comprise a heating module and a micromixer.

In a further implementation of the device according to the first aspect, the device further comprises one or more light emitters configured to irradiate the microfluidic fluid duct.

The light emitters can be configured to lead to a heating of the peptide hydrogel without heating other components or can be used to initiate a chemical process for faster gelation. In particular, the fluid duct can be surrounded by transparent material, such that the light from the light emitters can pass through to the fluid duct or the light can be focused at the end of the nozzle outlet.

In a further implementation of the device for printing a 3D object according to the first aspect, the light emitters comprise a first LED with a first wavelength and a second LED with a second wavelength different from the first wavelength.

The device can be configured to separately switch the first and second LED. Thus, different components in the fluid duct that have different light absorption spectra can be heated or activated separately.

In a further implementation of the device for printing a 3D object according to the first aspect, the bioink solution comprises one or several peptides, said peptides preferably having a general formula selected from:

   a)

and

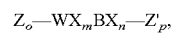   b)

wherein Z is an N-terminal protecting group and Z' is a C-terminal protecting group, with o and p being independently selected from 0 and 1;

wherein X is, independently at each occurrence, an aliphatic amino acid selected from isoleucine, norleucine, leucine, valine, alanine, glycine, homoallylglycine and homopropargylglycine with n and m being integers being independently selected from 0, 1 and 2, with the proviso that $m+n \leq 2$, wherein B is an aromatic amino acid selected from phenylalanine and tryptophan, or is an aliphatic counterpart of said aromatic amino acid, said aliphatic counterpart being selected from cyclohexylalanine, 4-hydroxy-cyclohexylalanine, 3,4-dihydroxycyclohexylalanine.

Wherein W is a polar amino acid selected from aspartic acid, glutamic acid, asparagine, glutamine, lysine, 5-N-ethyl-glutamine (theanine), citrulline, thio-citrulline, cysteine, homocysteine, methionine, ethionine, selenomethionine, telluromethionine, threonine, allothreonine, serine, homoserine, tyrosine, histidine, arginine, homoarginine, ornithine, lysine, N(6)-carboxymethyllysine, histidine, 2,4-diaminobutyric acid (Dab), 2,3-diaminopropionic acid (Dap), and N(6)-carboxymethyllysine, wherein said polar amino acid is preferably selected from the group consisting of aspartic acid, asparagine, glutamic acid, glutamine, serine, threonine, methionine, arginine, histidine, lysine, ornithine (Orn), 2,4-diaminobutyric acid (Dab), and 2,3-diaminopropionic acid (Dap).

Examples for such peptides are IVZK, IVFK, IVYK, FIVK and others. Alginates may also be used.

Experiments have shown that these components are particularly suitable for 3D printing.

A second aspect of the invention refers to a method for printing a 3D object, preferably an in situ method for printing a 3D object. The method comprises:

mixing a bioink solution, in particular a peptide solution, a cell culture medium and a buffer solution capable of inducing gelation of the bioink solution to obtain a hydrogel, in particular a peptide hydrogel, and ejecting the hydrogel, in particular the peptide hydrogel, out of a nozzle to build the 3D object.

The methods according to the second aspect of the invention can be performed by the device for printing a 3D object according to the first aspect of the invention. Further features or implementations of the method according to the second aspect of the invention can perform the functionality of the device for printing a 3D object according to the first aspect of the invention and its different implementation forms.

In a first implementation of the method for printing a 3D object of the second aspect, the mixing is performed in fluid duct, in particular a microfluidic channel, wherein preferably the nozzle comprises the fluid duct.

The fluid duct can comprise elements within the fluid duct which lead to an improved mixing between the components. For example, the elements can be configured to create turbulences within the fluid duct, which may lead to an improved mixing.

In a second implementation of the method for printing a 3D object of the second aspect as such or according to the first implementation of the second aspect, the nozzle comprises the microfluidic fluid duct.

In a third implementation of the method for printing a 3D object of the second aspect as such or according to any of the preceding implementations of the second aspect, air pressure and/or microfluidic pumps are used to eject the peptide hydrogel.

In a fourth implementation of the method for printing a 3D object of the second aspect as such or according to any of the preceding implementations of the second aspect, the method further comprises an initial step of scanning a 3D source object.

By obtaining a 3D scan of the 3D source object, the method can create a target object that closely resembles the source object, thus acting as 3D copying method.

In a fifth implementation of the method for printing a 3D object of the second aspect as such or according to any of the preceding implementations of the second aspect, the cell culture media comprises a plurality of cell types.

In a further implementation of the method for printing a 3D object of the second aspect, the dispersion comprises micro and/or nanoparticles, preferably peptide microparticles, peptide nanoparticles, silver nanoparticles, gold nanoparticles, nanowires, quantum dots and/or carbon nanotubes.

In a preferred embodiment, the method of the present invention is carried out under physiological conditions.

The buffer solution capable of inducing instantaneous gelation used in the method of the invention can be phosphate buffer saline or buffer(s) containing salt(s), such as sodium chloride or calcium chloride.

In one implementation of the in situ method for printing a 3D object, the bioink solution is a peptide solution as defined herein above.

A further aspect of the invention refers to a method of obtaining a hydrogel, the method comprising:
  providing a bioink solution, in particular a peptide solution, through a first inlet (410) into a first airbrush (401),
  providing a buffer solution capable of inducing instantaneous gelation of the bioink solution to a hydrogel, in particular a peptide hydrogel, through a second inlet (420) into a second airbrush (402), and
  air-spraying the bioink solution and the buffer solution simultaneously through the nozzles (411, 421) of said first and said second airbrush (401, 402), onto the same site on a surface, thereby creating the hydrogel, in particular the peptide hydrogel.

In a first implementation of the method of obtaining a hydrogel, the bioink solution is a peptide solution as defined herein above.

In a further implementation of the method of obtaining a hydrogel, the buffer solution capable of inducing instantaneous gelation is phosphate buffer saline or buffer(s) containing salt(s), such as sodium chloride or calcium chloride.

In a further implementation of the method of obtaining a hydrogel, the airbrushes are used with a device as defined herein above as first aspect of the invention.

The airbrushes can be used with a device according to the present invention as defined herein.

The airbrushes can also be used as a hand held device.

The bioink solution and the buffer solution are preferably directly sprayed onto a surface, such as a wound site, where the hydrogel forms.

In particular, the airbrush can be used with a device such as a robotic arm as shown in FIGS. 4A, 4B and 4C for direct spray of a peptide hydrogel onto a surface such as a wound site. The air brush assembly can also be used as a hand held device to directly spray the peptide hydrogels onto a surface such as a wound site.

BRIEF DESCRIPTION OF THE DRAWINGS

To illustrate the technical features of embodiments of the present invention more clearly, the accompanying drawings provided for describing the embodiments are introduced briefly in the following. The accompanying drawings in the following description are merely some embodiments of the present invention, modifications on these embodiments are possible without departing from the scope of the present invention as defined in the claims.

FIG. 3A is a schematic representation of the device/nozzle developed for 3D bioprinting of peptide bioinks, as also shown in FIG. 1A.

FIG. 3B is a schematic representation of the device/nozzle including a micromixer (240) that can be used to enhance mixing of the peptide and cells to get a more homogeneous distribution of the cells across the 3D bioprinted construct.

FIG. 4 B Robotic arm 3D bioprinting set-up. The figure shows a schematic picture of robotic 3D bioprinter inside the biosafety cabinet showing microfluidic pumps, robotic arm and printing nozzle. All the bioprinting experiments were performed inside the biosafety cabinet.

FIG. 4C Scheme of the bioprinting nozzle installed on a commercially available dual arm robotic system and integrated with microfluidic pumps to create 3D structures. The 3D scanner scans the structure and sends the information to a computer where a software reconstructs the image of the 3D structure. The robotic arms then move the nozzles according to the design of the 3D structure to create the final 3D shape. The stage is temperature controlled and flexible to move into different directions and can also rotate in different directions.

FIGS. 6A and 6B are fluorescence confocal microscopy 2D and 3D images of human skin fibroblast cells bioprinted using peptide-based bioink (IVZK).

FIG. 8A shows in-situ generated silver nanoparticles inside the 3D bioprinted IVZK peptide bioink. 1 mM silver nitrate solution was mixed with IVZK bioink and after bioprinting UV exposure was done for 10 min at 254 nm. Yellowish colour of the bioprinted text is due to the formation of silver nanoparticles.

FIG. 8B, C shows the transmission electron microscopy (TEM) images of silver nanoparticles. The average diameter calculated from the TEM images using imageJ was 4.4 nm.

FIG. 8D, E 3D bioprinted IVZK peptide bioink after inclusion of green colour quantum dots in the peptide solution without (D) and with (E) UV excitation at 365 nm.

FIG. 8F confocal microscopy image showing the emission from green color quantum dots which adsorb on the peptide fibers inside the scaffold and clearly showing the fibrous network of 3D bioprinted peptide bioink (IVZK).

FIG. 11A Fluorescence confocal microscopy images of 3D bioprinted HDFn cells using IVFK, IVZK, and alginate-gelatin bioinks at different days of cell culturing (nucleus is shown in blue, F-actin is shown in red and vinculin is shown in green).

FIG. 11B Picture of hydrogels printed on day 1 and on day 21 after cells had been cultured in the media for 21 days.

FIG. 11C 3D cell viability assay of HDFn cells 3D bioprinted in IVFK, IVZK, and alginate-gelatin bioinks at various time points.

FIG. 12A Fluorescence confocal microscopy images of 3D bioprinted human bone marrow-derived mesenchymal stem cells (BM-MSCs) cells using IVZK and alginate-gelatin bioinks at different days of cell culturing (nucleus is shown in blue, F-actin is shown in red and vinculin is shown in green).

FIG. 12B 3D cell viability assay of BM-MSCs cells 3D bioprinted in IVZK and alginate-gelatin bioinks at various time points.

DETAILED DESCRIPTION OF EMBODIMENTS

Figure 1:
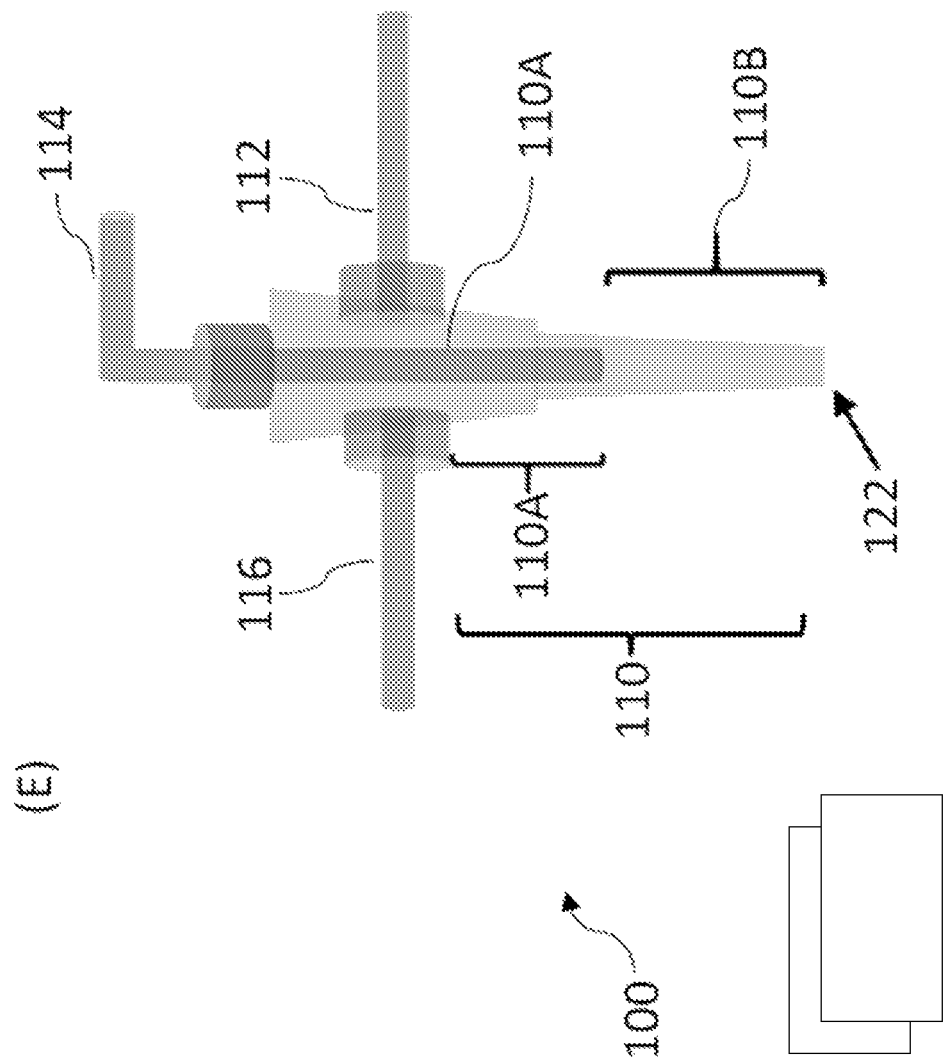
FIG. 1A is a schematic of a peptide hydrogel formation using a 3D bioprinter, FIG. 1B are two pictures of the microfluidic printing nozzle containing three different inlets that can be connected to the microfluidic pumps.
FIG. 1C shows the microfluidic printing device in a specially designed holder fitted on a robotic arm.
FIG. 1D shows a printed structure containing IVZK peptide bioink and human skin fibroblast cells using the 3D bioprinter.
FIG. 1E is a schematic of a device for building a 3D object.

FIG. 1A is a schematic illustration of a peptide hydrogel formation using a 3D bioprinter. A bioink solution and cell culture media containing different cell types mix together in a first region. The mixture is then mixed with a buffer solution in a second region, which is a microfluidic fluid duct, to induce gelation and form the peptide hydrogel. The peptide hydrogel is then ejected out through outlet nozzle. The buffer solution can be a phosphate buffer solution, e.g. a phosphate buffer saline (PBS).

Benefit of using peptide bioinks for biological applications include their resemblance to natural, body-like features compared to non body-like materials (e.g. polymers) or natural, but not from human background, and undefined material (alginate from crustaceae, plants, etc.) with significant batch-to-batch variations which will has an impact on the sustainability of the bioprinted 3D structures. Also, biofunctionalization can be more smoothly fitted and added to a peptide compound than to a polymer structure. Peptide bioinks also allow addition of different materials (peptide micro or nanoparticles, gold or silver nanoparticles, nanowires, graphene, carbon nanotubes and quantum dots, for example) and subsequent printing in 3D structures that can perform various functions. For example, the built structures can be used for imaging, sensing, drug delivery, catalysis and tuning of the mechanical properties of the peptide hydrogel.

FIG. 1B is a picture of the microfluidic printing nozzle containing three different inlets that can be connected to the microfluidic pumps. The cells were pre-loaded in the tubing loop with inner diameter of 250 µm connected with the nozzle in order to get a uniform distribution of the cells throughout the 3D construct.

FIG. 1C shows the microfluidic printing device in a specially designed holder fitted on a commercially available robotic arm that can print 3D structures. The nozzle needle close to the petri dish is used to print the peptide hydrogel bioink into a 3D circle.

FIG. 1D shows a printed structure containing IVZK peptide bioink and human skin fibroblast cells using the 3D bioprinting device.

FIG. 1E shows in detail a device 100 for building a 3D object. The device comprises three inlets 112, 114, 116 for taking in a bioink solution, a phosphate buffer saline and a dispersion, e.g. a cell culture medium. The three inlets 112, 114, 116 are connected to a fluid duct 110, which comprises a first part 110A and a second part 110B. The bioink solution from the first inlet 112 and the dispersion from the third inlet 116 are brought together in the first part 110A. The mixture of these two components is then pushed through the second part 110B and meets the phosphate buffer solution from the second inlet 114. The second part 110B forms a microfluidic fluid duct towards an outlet nozzle 122 where the mixture is ejected from the device 100. The term fluid duct herein refers to any tube, canal, pipe, or conduit by which the bioink and the other components can be conducted or conveyed and mixed with the other component or components.

Figure 2:
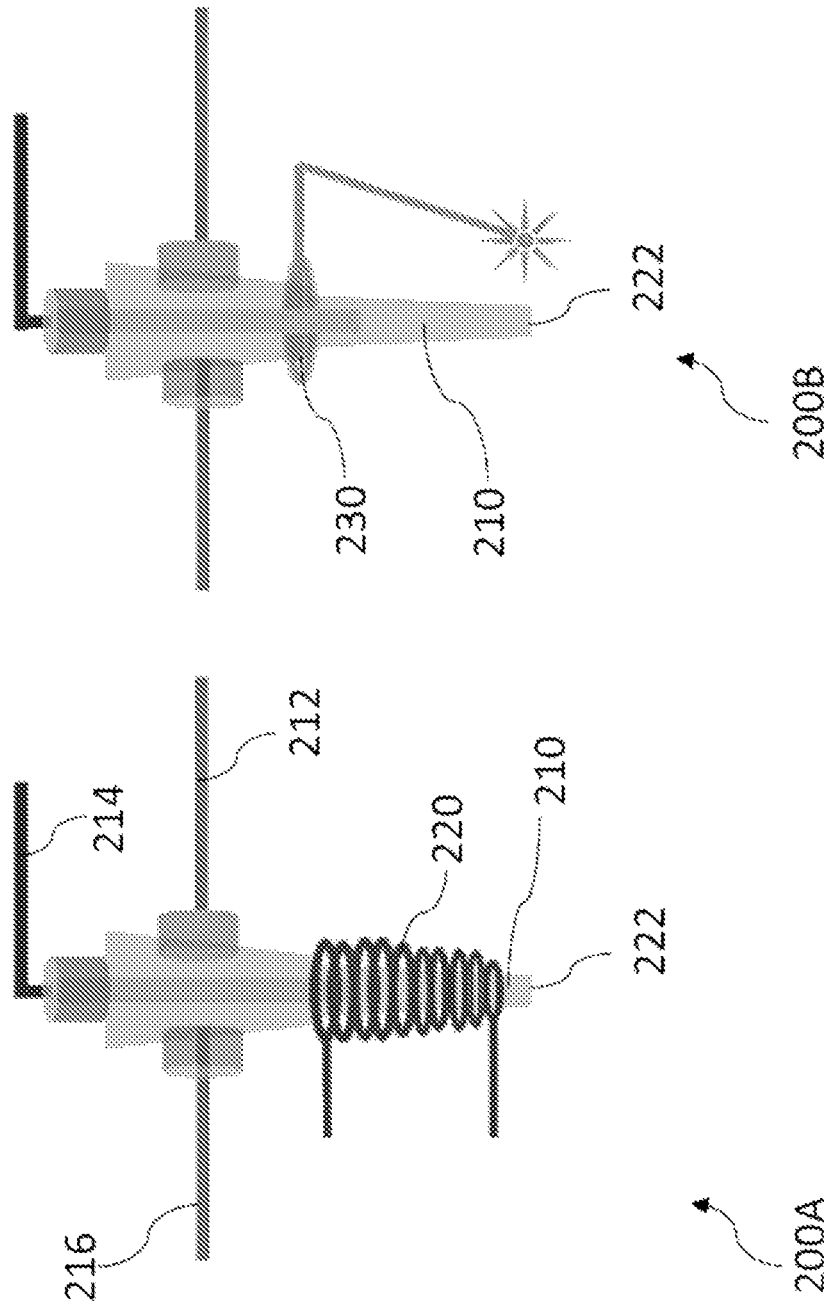
FIG. 2 shows two devices for building a 3D object, wherein the first device comprises a heating unit and the second device comprises a light treatment module.

FIG. 2 shows two devices 200A, 200B for building a 3D object. Both devices comprise a first inlet 212 for taking in a bioink solution, a second inlet 214 for taking in a phosphate buffer saline and a third inlet 216 for taking in different cell types dissolved in a cell culture media. The devices 200A, 200B also comprise a fluid duct 210 which is arranged within the nozzle 222. The fluid duct 210 receives the bioink solution, the phosphate buffer saline and the cell culture media. The three components are mixed within the fluid duct to obtain a peptide hydrogel. The peptide hydrogel is then ejected from the outlet of the nozzle 222.

The first device 200A comprises a heating unit 220, which comprises a heating wire which is wrapped around the nozzle 222 and thus around the fluid duct 210.

The second device 200B comprises a light emitter 230 which is configured to irradiate the fluid duct 210 within the nozzle. The nozzle 222 is completely made of transparent material. In other embodiments, only a part of the nozzle 222 is transparent so that the light emitter can irradiate material within the fluid duct.

Figure 3:
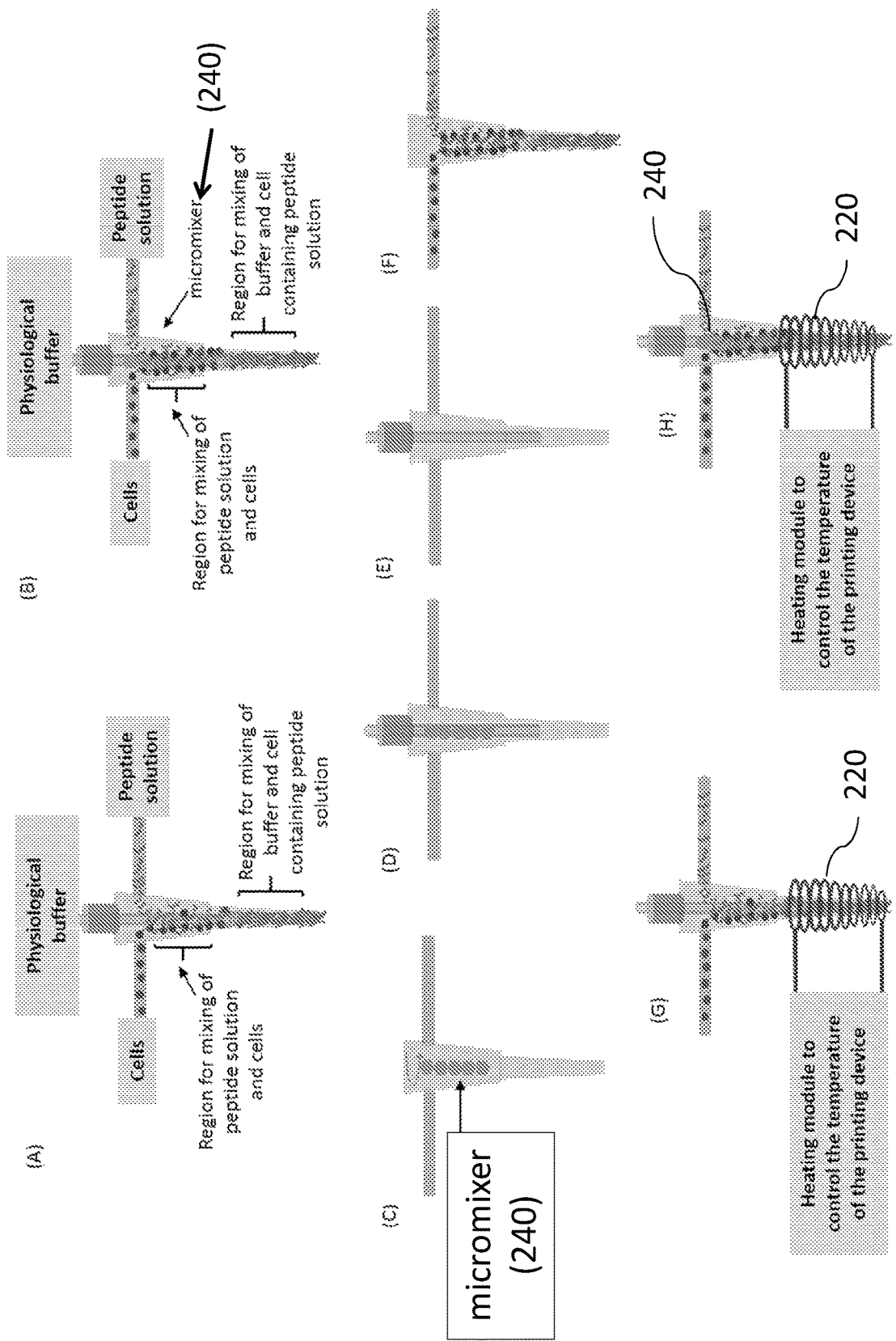
FIG. 3 C-H shows a breakdown of the different regions of the device/nozzle, namely:
  (C) with the micromixer (240) and the main nozzle,
  (D) with the micromixer (240), the buffer nozzle and the main nozzle,
  (E) with the buffer nozzle and the main nozzle,
  (F) with mixing of the cells, peptides and the buffer to form the hydrogel, (G) and (H) with the microheater (220) on the device/nozzle (A) and (B), to control the temperature of the peptide gelation process, if necessary.

FIG. 3 shows different designs of the devices/nozzles. Two types of devices/nozzles can be used to perform 3D bioprinting of peptides. The device/nozzle 1 (FIG. 3A, also shown in FIG. 1A) contains two regions of mixing. In the first region, the peptide solution and cells in cell culture media were mixed, and in the second region, PBS was introduced to induce instant gelation of the peptide which results in the encapsulation of the cells into the peptide hydrogel (FIG. 3A). In principle, any cell type can be used for 3D bioprinting using this method. The device/nozzle 2 (FIG. 3B) contains a micromixer (240) that can be used to enhance the mixing between peptide and cells to get a more homogeneous distribution of the cells inside the 3D construct. FIG. 3C-F show more details of different regions of the device/nozzle. FIG. 3G and FIG. 3H show the assembly of the microheater (220) on the devices/nozzles shown in FIG. 3A and FIG. 3B to control the temperature of the devices/nozzles.

Figure 4:
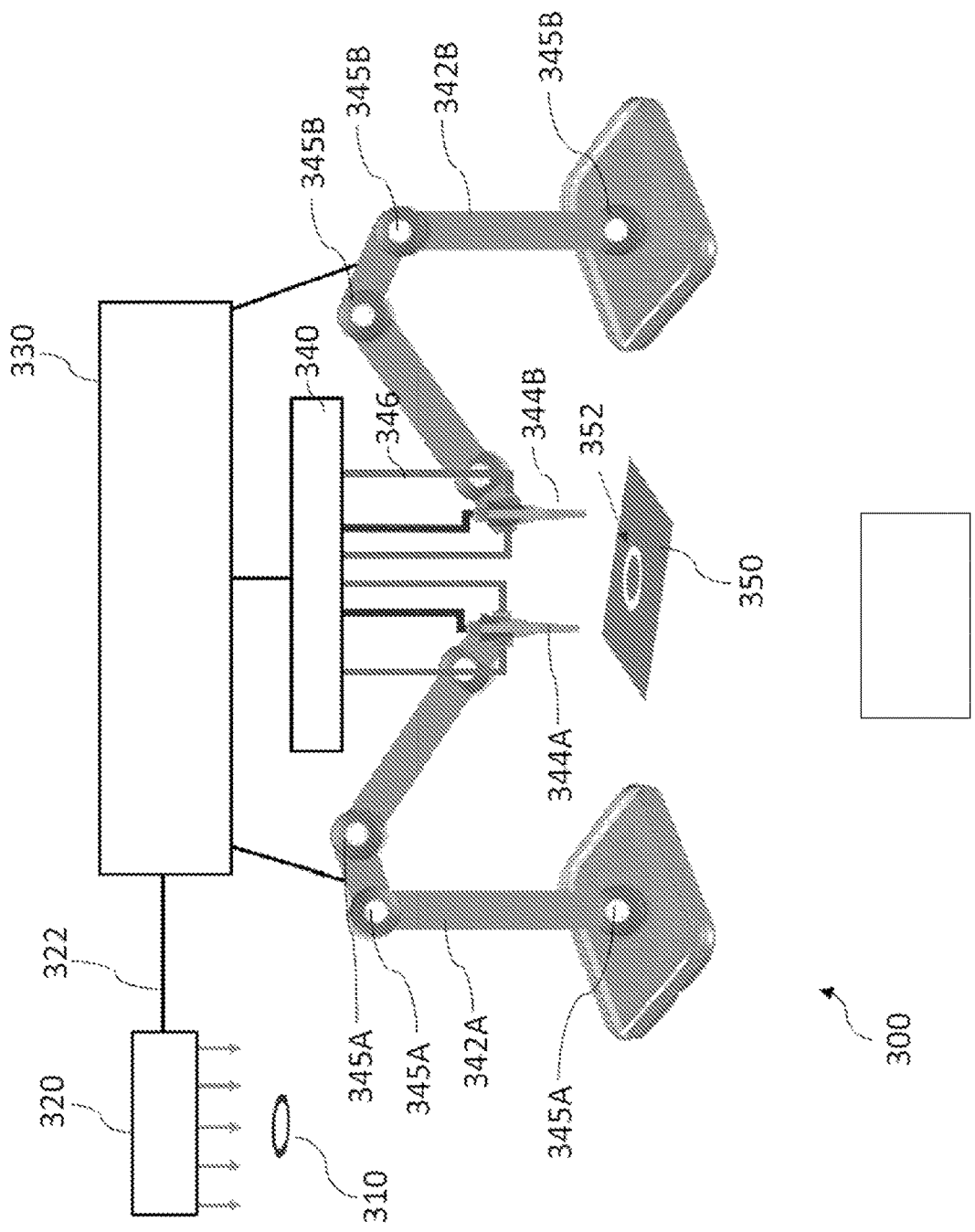
FIG. 4 A is a schematic illustration of a 3D bioprinter platform containing multiple robotic arms equipped with multiple nozzles for printing of different peptides or cell types.
Figure 4:
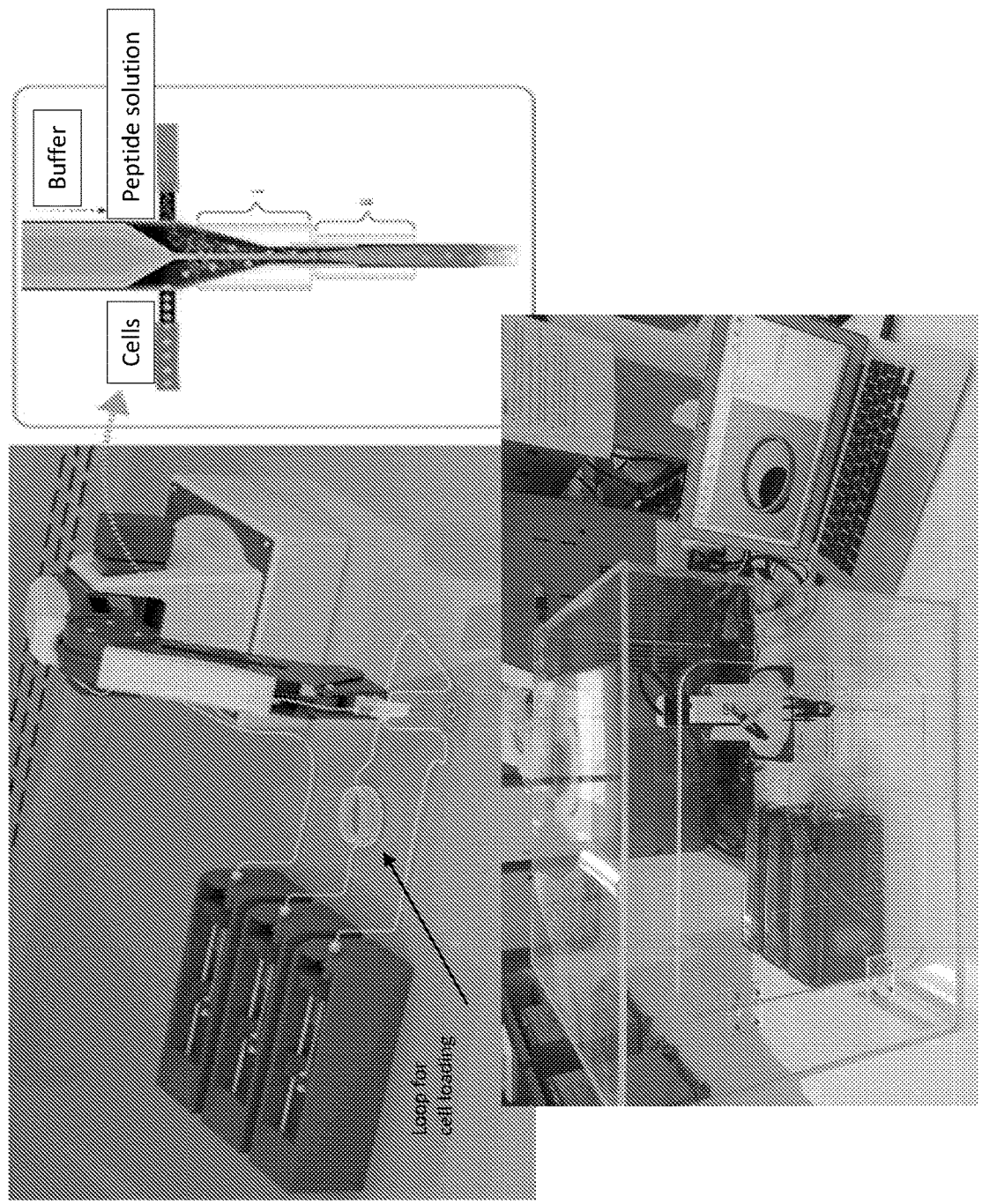
Figure 4:
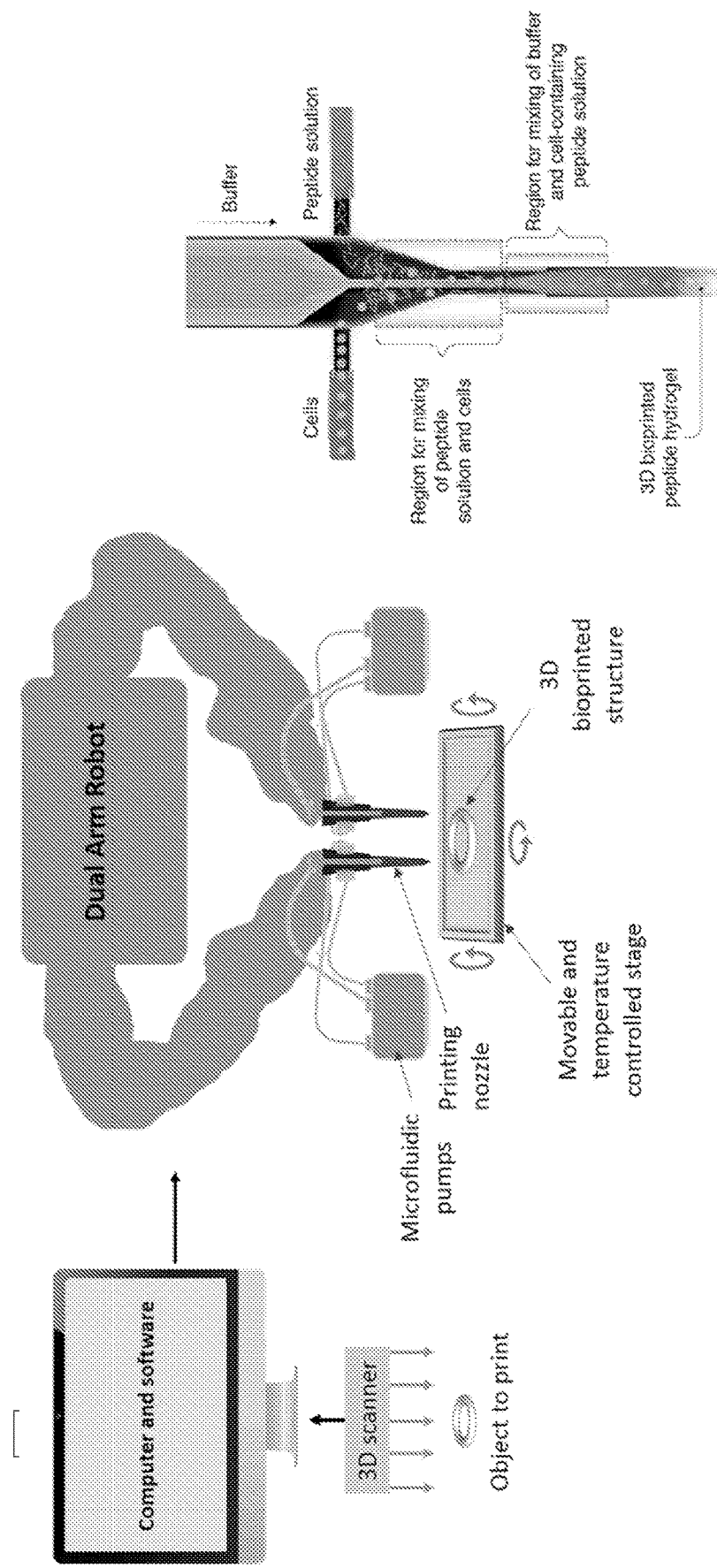

FIG. 4A is a schematic illustration of a 3D bioprinting platform 300 comprising two robotic arms 342A, 342 that are equipped with printing devices 344A, 344B for printing of different peptides or cell types. The printing devices 344A, 344B shown in FIG. 4A can be implemented as shown in FIG. 2.

The 3D bioprinting platform 300 comprises a 3D scanner 320 that is configured to scan an object 310 to be printed. After scanning the object 310, the 3D scanner transmits a representation 322 of the object to a control module 330 for controlling the robotic arms 342A, 342B, microfluidic pumps 340 and printing devices 344A, 344B. The printing devices 344A, 344B are arranged to print the target object 352 on an automated stage 350 with heating and cooling. The automated stage 350 can comprise multiple holders to print e.g. in a petri dish or multiple well plates. It should be noted that the 3D printing and the device and method in accordance with the present invention is not limited to any particular or specific 3D pattern or 3D object. It can be used for any 3D object.

The printing devices 344A, 344B are connected to the microfluidic pumps through flexible tubes 346. There is one tube for each of the three components, such that the components can be mixed in the printing devices 344A, 344B.

In other embodiments, a single robotic arm can be equipped with multiple nozzles. Only two robotic arms are shown in FIG. 4A. Additional robotic arms can be included to print multiple cell types.

The printing platform 300 can be used in combination with peptide-based bioinks and allow a continuous printing of different cell types or other biological compounds into 3D structures with excellent biocompatibility.

The printing process can be based on using microfluidic pumps or air pressure to move the bioink solution, phosphate buffer saline (PBS) and different cell types (human skin fibroblast cells, for example) in cell culture media into individual fluid ducts, and after mixing, the peptide-based hydrogel containing the cells extruded from the nozzle or outlet for 3D bioprinting.

The robotic arms 342A, 342B move according to the 3D design in X, Y and Z direction to print the object information sent by the 3D scanner using peptide bioink extruded from the nozzle. A combination of two to three or more robotic arms can be used to print multiple peptide bioinks in parallel or one by one to print multiple cell types at the same time or different time intervals. Moreover, on one robotic arm, e.g. two or three nozzles can be attached to print 3D structures. This way, multiple cellular functionalities can be introduced in a single 3D bioprinted structure which is a requirement for a fully functional organ/tissue construct.

The robotic arms 342A, 342B each comprise four hinges 345A, 345B, thus allowing a high degree of flexibility when positioning the printing devices 344A, 344B.

Currently available 3D bioprinters are mainly based on linear systems, such as inkjet bioprinter systems, which are limited to 3-dimensional xyz movement. Thus, they offer 3 degree of freedoms (DOF) or an 3-axis system. Robotic systems have the advantage over linear systems to increase flexibility by increasing the number of DOFs. Robotic systems can start from 3-axis robots, to 4-axis robots and so forth, up to 7-axis robots. The system of FIG. 4A has two robotic arms thus giving additional degrees of freedom and allowing for supplementary angular movements when compared to a linear system or a one robotic arm system. In a variation of the system of FIG. 4A, where the base of the robotic arm can also rotate around itself, an increase in flexibility to a 13- or 14-axis printing system is achieved.

Since the robotic arms incorporate swift rotational movements, the system allows for faster and smoother printing. The quality of the printed biomaterial is enhanced due to the additional degrees of freedom. Multiple robotic arms can be equipped with multiple nozzles for printing of different types of bioinks or cell types. Robotic arms are also more compact in size than existing 3D bioprinters and can be more easily transported. This gives transport advantages of the printer when the operating procedures will take place at different surgical rooms. The system can be used for example for application toward plastic, reconstructive and aesthetic surgery.

FIG. 4B shows another integration of the device/nozzle on a commercially available robotic arm and using pumps.

Human skin fibroblast cells together with IVZK and IVFK peptide solutions were 3D bioprinted using this set-up as a further example.

In more detail, a robotic arm 3D bioprinter was used to perform 3D bioprinting of normal human skin fibroblast cells (HDFn). The bioprinter was developed by integrating microfluidic pumps, a printing nozzle, and a robotic arm (FIG. 4B). A commercially available robotic arm 3D printer (Dobot Magician, Dobot) was converted to a bioprinter by exchanging the polymer extruder of the robotic arm with the bioprinting nozzle. The microfluidic printing nozzle was prepared by using two different syringe needles with different internal diameters (FIG. 4B). The main needle (18 Gauge) has the internal ID=840 µm, and the top needle has an internal diameter of 80 µm (34 Gauge) and the outer diameter of 190 µm. Two holes were created at the side of the main needle, and PTFE tubing (PTFE #30 AWG thin wall tubing, Cole Parmer) with an internal ID of 304 µm was inserted from one side of the main nozzle by creating a hole of the same size as of the PTFE tubing's outer diameter for the flow of the cells. On the other side of the needle, PTFE tubing (PTFE #24 AWG thin wall tubing, Cole Parmer) with an internal ID of 550 µm was inserted and used for the flow of peptide solution. A transparent epoxy was used to seal the tubing and the top nozzle. The printing nozzle has three inlets and one outlet. A combination of different diameter needles can also be used to prepare different printing nozzles with different diameters. The tubing for the peptide solution and cell culture media (containing different cell types) inlets were inserted into the side wall of the main needle so that both the fluids can mix in this region. The second needle (34 G) was inserted inside the main needle (18 Gauge) from the top such that the solution from this needle (10×PBS) mixes with other two solutions to make the peptide hydrogel close to the end of the main needle. The length of the main needle was 2.5 cm and the mixing region for the buffer with the cells and peptide was approximately 2.0 cm. The mixing region for the buffer with the cells and peptide can be adjusted to make the peptide hydrogel. The length 2.0 cm can be varied depending on the formation of the peptide hydrogel inside the nozzle.

A further set-up using a commercially available dual arm robotic system that is integrated with microfluidic pumps to create 3D structures is shown in FIG. 4C. The 3D scanner scans the structure and sends the information to a computer where a software reconstructs the image of the 3D structure. The robotic arms then move the nozzles according to the design of the 3D structure to create the final 3D shape. The stage is temperature controlled and flexible to move into different directions and can also rotate in different directions.

Figure 13:
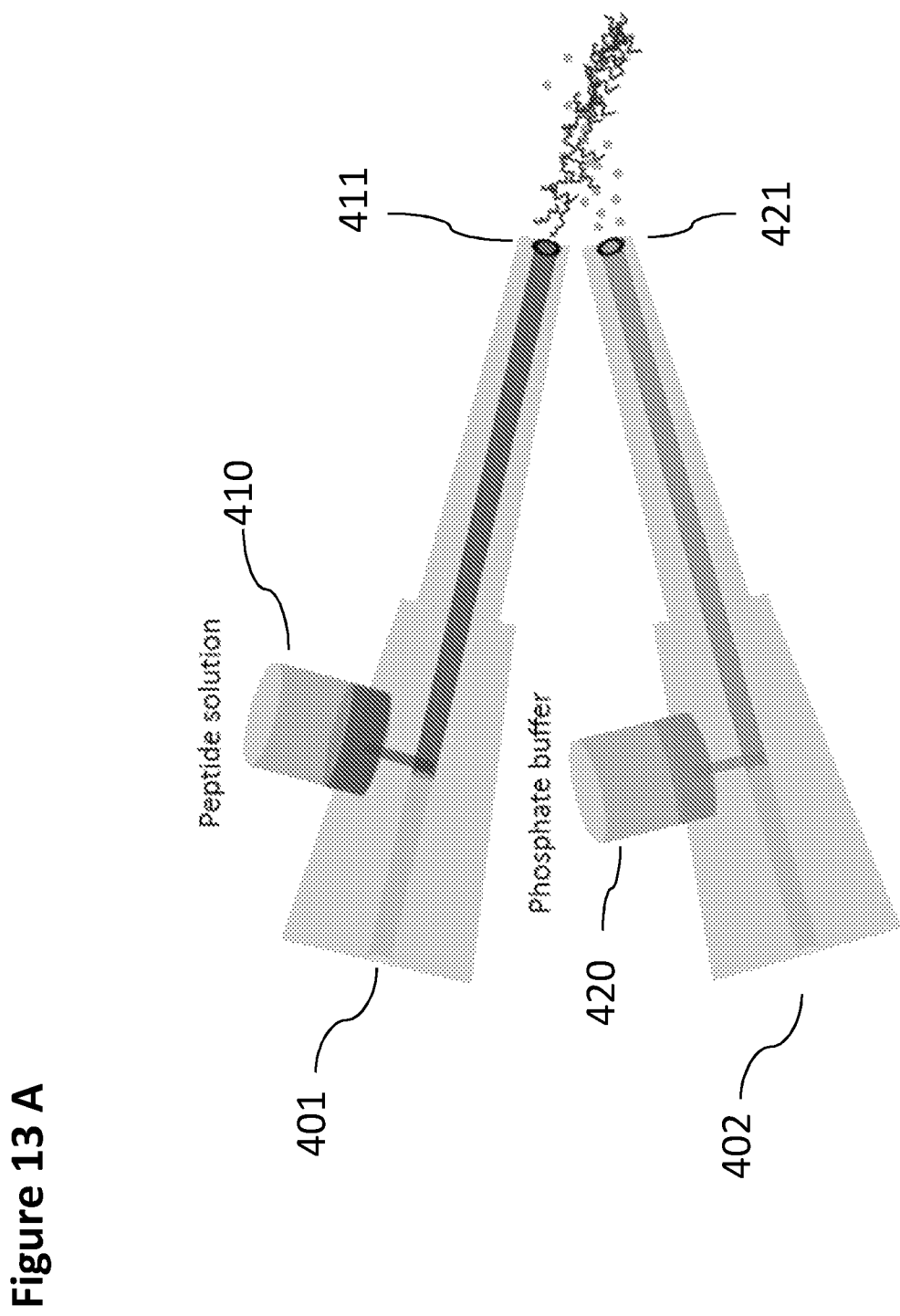
FIG. 13A Schematic presentation of the mode of action to spray both peptide and phosphate buffer using the air brush. The nozzles of the air brushes are aligned at an angle such that both the peptide solution and phosphate buffered saline (PBS) streams, coming out from the nozzles, combine at a certain point to create the peptide hydrogel.
FIG. 13B Pictures of two air spray brush nozzles that were assembled in a casing made from Perspex sheet at an angle such that the stream from both the nozzles meet at one point. One nozzle contained the peptide solution (5 mg/ml IVZK) and the second nozzle contained the phosphate buffer solution (10×).
FIG. 13C Scanning electron micrographs (SEM) of peptide hydrogel sprayed on a silicon surface. The SEM images confirmed the formation of the peptide fiber network.
Figure 13:
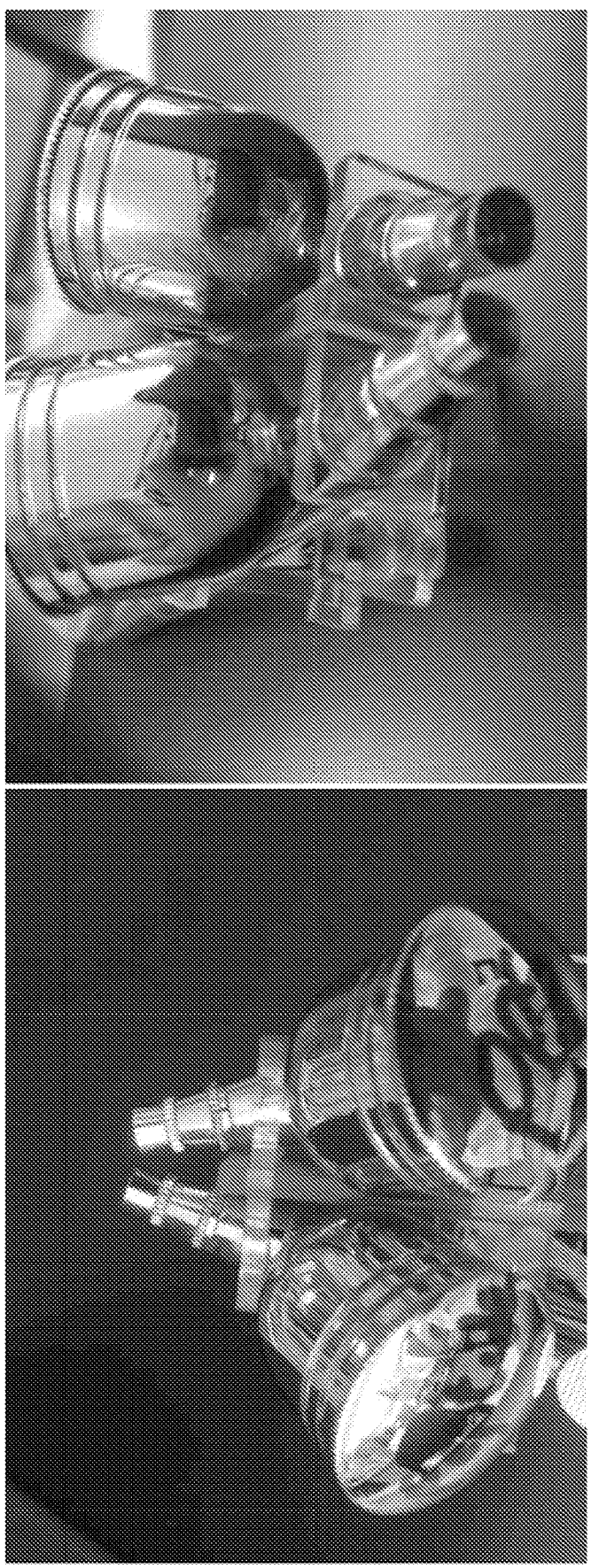
Figure 13:
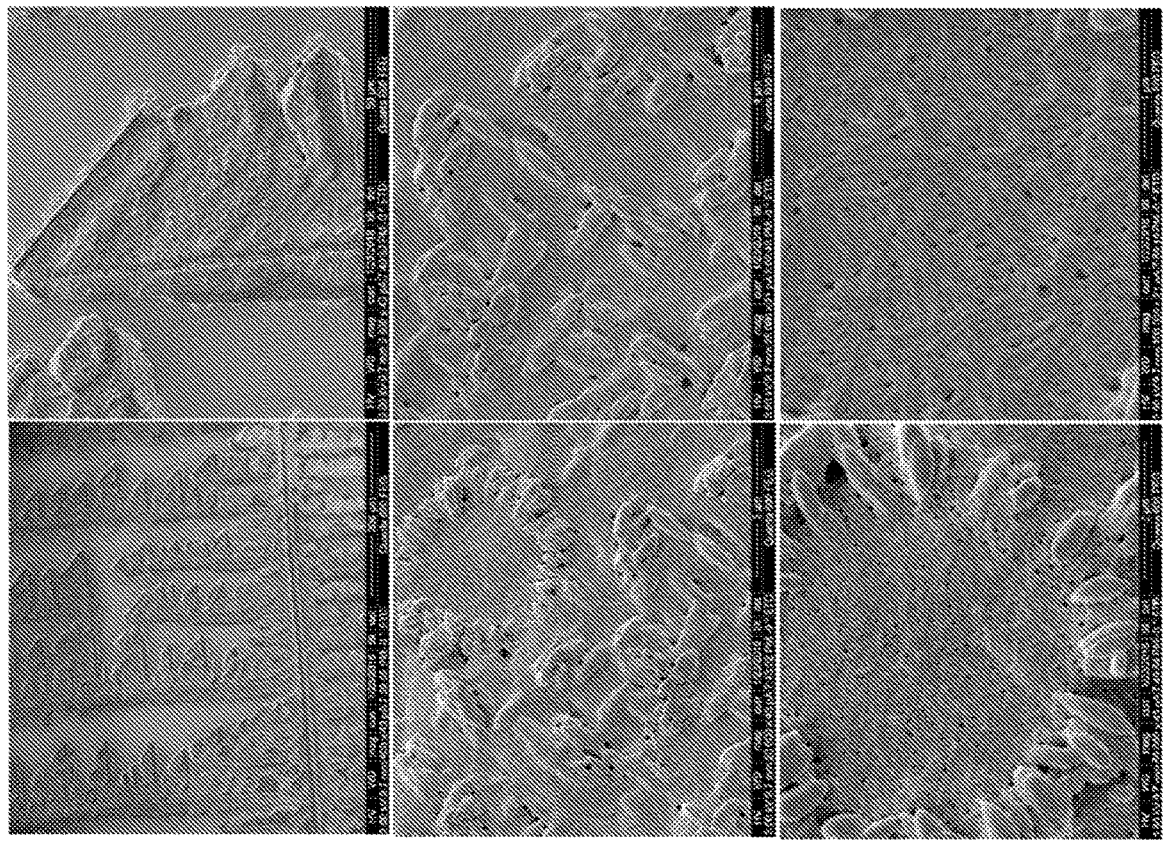

In addition, the peptides such as IVZK and IVFK can also be sprayed directly onto different surfaces using a combination of air spray nozzles. FIG. 13A shows the schematic of the system in which two airbrush nozzles were used to spray at an angle so that both the solutions (peptide and phosphate buffer saline) meet on a certain point to form peptide hydrogel. FIG. 13B shows examples of such air spray nozzles. FIG. 13C shows the scanning electron microscopy (SEM) images of the IVZK peptide sprayed on a silicon wafer. The SEM images clearly showed the formation of the peptide fiber networks using the air spray nozzles. The spray nozzles can be incorporated on a robotic arm system, such as the ones shown in FIG. 4A to C, to directly coat different peptides either alone or in combination with different types of cells on a wound surface in an automated way. The spray nozzles can also be used as a handheld device to directly spray on a wound.

Experiments have been performed to show the technical examples using the 3D/4D bioprinting method.

Preparation of Peptide and Phosphate Buffer Solutions

All the peptide (Bachem, Germany) solutions were freshly prepared by dissolving different amounts of the peptides (IVFK and IVZK) in 1 ml of Milli-Q water and mixed for 30 seconds by vortexing to obtain a homogenous solution. In this example, 15 mg of each peptide was dissolved in Milli-Q water. The phosphate buffered saline (PBS, 10× concentration) was obtained from Sigma and used as received in the printing process.

The relative molecular mass of the IVFK and IVZK peptides was 546.71 and 552.76 with a purity of 97.1% and 97.2% (determined by HPLC method), respectively.

Cell Culture

Human dermal fibroblasts, neonatal (HDFn, C0045C) were purchased from Thermo Fisher Scientific, USA. These cells were first cultured using medium 106 (Thermo Fisher Scientific, USA) supplemented with 10% fetal bovine serum and 1% penicillin/streptomycin. T175 or T75 cell culture flasks (Corning, USA) were used to maintain the cells in a humidified incubator with 95% air and 5% $CO_2$ at 37° C. The cells were subcultured by trypsinization at approximately 80% confluence. The cell culture media was replaced every 48 hours.

Fabrication of the Microfluidic Printing Nozzle

The microfluidic printing nozzle was prepared by using four different syringe needles with different internal diameters, selected from 100 µm, 150 µm, 230 µm, 300 µm, 450 µm, 500 µm, 600 µm, 700 µm, 800 µm, 1 mm and 1.2 mm diameters. The printing nozzle has three inlets and one outlet. A combination of different diameter needles can be used to prepare different printing nozzles with different diameters, depending on the individual solutions (viscosity) or depending on the writing structures giving rise to thinner or broader printed structures. Two holes were created on the two sides of the middle needle containing the outlet. The needles for the peptide solution and cell culture media (containing different cell types) inlets were inserted into the main needle so that both the fluids can mix together in this region. The third needle with a particular length was inserted from the top such that the solution from this needle (10× PBS) mixes with other two solutions to make the peptide hydrogel.

Printing Procedure

The printing involves three different components such as peptide solution, phosphate buffer saline (PBS) and different cell types. As for peptides, solutions of different concentrations of IVZK or IVFK peptides were prepared by weighing different amounts of the peptide (15 mg, for example) and dissolved in 1 ml Milli-Q water. The second solution contained 10×PBS. The third solution contained primary human skin fibroblast cells in cell culture media (four million cells in 500 µl of the DMEM cell culture media, for example). Primary human skin fibroblast cells were used to demonstrate cell printing. Other cell types can be incorporated in the printing process similarly as described in the case of primary human skin fibroblasts. All three solutions were pumped to the nozzle using the syringe pumps at different flow rates. The flow rates were adjusted so that three solutions meet at the interface which causes gelation of the bioink and peptide hydrogel come out from the outlet of the printing nozzle. In a particular experiment, flow rates used were 20 µl/min for cell culture media containing skin fibroblast cells, 25 µl/min for the peptide solution and 20 µl/min for the 10×PBS. A simple ring structure was printed by the deposition of peptide hydrogel in a layer-by-layer fashion with a diameter of about 10 mm and thickness about 2 mm. Different structures, for example, circle and square and grid were printed instantaneously by using the movement of a 3D printer or a robotic arm 3D printer.

Figure 5:
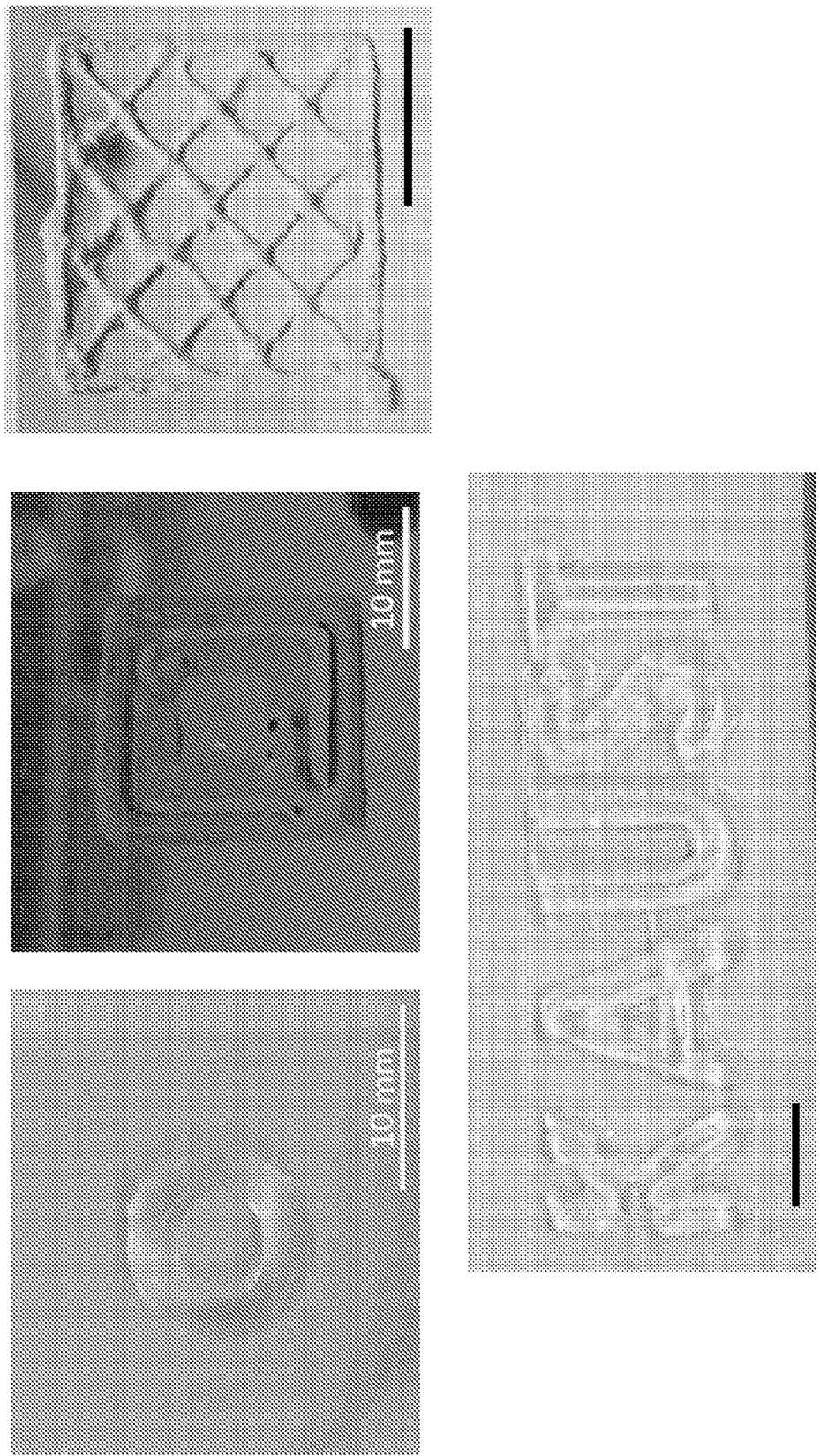
FIG. 5 illustrates the printability of peptide-based bioinks (IVFK and IVZK) into different shapes such as circle, square, grid and letters/text. The scale bar in all figures is 10 mm.

FIG. 5 shows the printability of peptide-based bioinks (IVFK and IVZK) into different shapes such as circle and square, grid or letters/text.

The constructs were printed onto 35 mm tissue culture petri dish. After bioprinting, the constructs were placed in biosafety cabinet for 3 min to further facilitate self-assembly of peptide bioinks. Then, the constructs were gently washed 2 or 3 times with culture medium. To each dish, 3 mL of culture medium was added and cultured in a humidified incubator at 37° C. and 5% $CO_2$. At pre-determined time points, the constructs were taken out to perform 3D assay and cytoskeletal staining of cells for fluorescence confocal microscopy studies.

Scanning Electron Microscopy (SEM) Analysis

For SEM analysis, the peptide hydrogel ring was directly 3D printed on a small piece of silicon wafer (20×20 mm). The sample was first fixed with 3.7% paraformaldehyde solution for 30 minutes. The peptide hydrogel ring was then washed with different concentrations of ethanol (10, 20, 30, 40, 50, 60, 70, 80, 90, 99.8%) sequentially to remove water from the hydrogel. The sample was dried in a critical point dryer to evaporate ethanol and to preserve the structure of the hydrogel. After this it was coated with 4 nm of Pt/Pd metals using a sputter coater. Finally, it was examined using Quanta 3D FEG SEM/FIB microscope and Magellan™ XHR SEM using an accelerating voltage of 10 kV and 2 kV, respectively.

Cytoskeletal Staining

Cytoskeletal staining of the 3D circular constructs containing human dermal fibroblast cells was performed at different time intervals after 1, 3, 7 and 14 days of culture. In brief, the 3D construct was treated with 3.7% paraformaldehyde solution for 30 minutes to fix the cells. After that it was incubated in a cold cytoskeleton buffer (3 mM MgCl2, 300 mM sucrose and 0.5% Triton X-100 in PBS solution) for 10 minutes to permeabilise the cell membranes. The permeabilised cells were incubated in blocking buffer solution (5% FBS, 0.1% Tween-20, and 0.02% sodium azide in PBS) for 30 minutes at 37° C., followed by incubation in FITC-phalloidin (1:200) for 1 hour at 37° C. Further, the construct was incubated in DAPI for 1 hour at 37° C. to counterstain the nuclei of the cells. Fluorescence confocal microscopy (Zeiss LSM 710 Inverted Confocal Microscope, Germany) was used to image the labelled human skin fibroblasts in the 3D construct (see FIG. 6).

Figure 9:
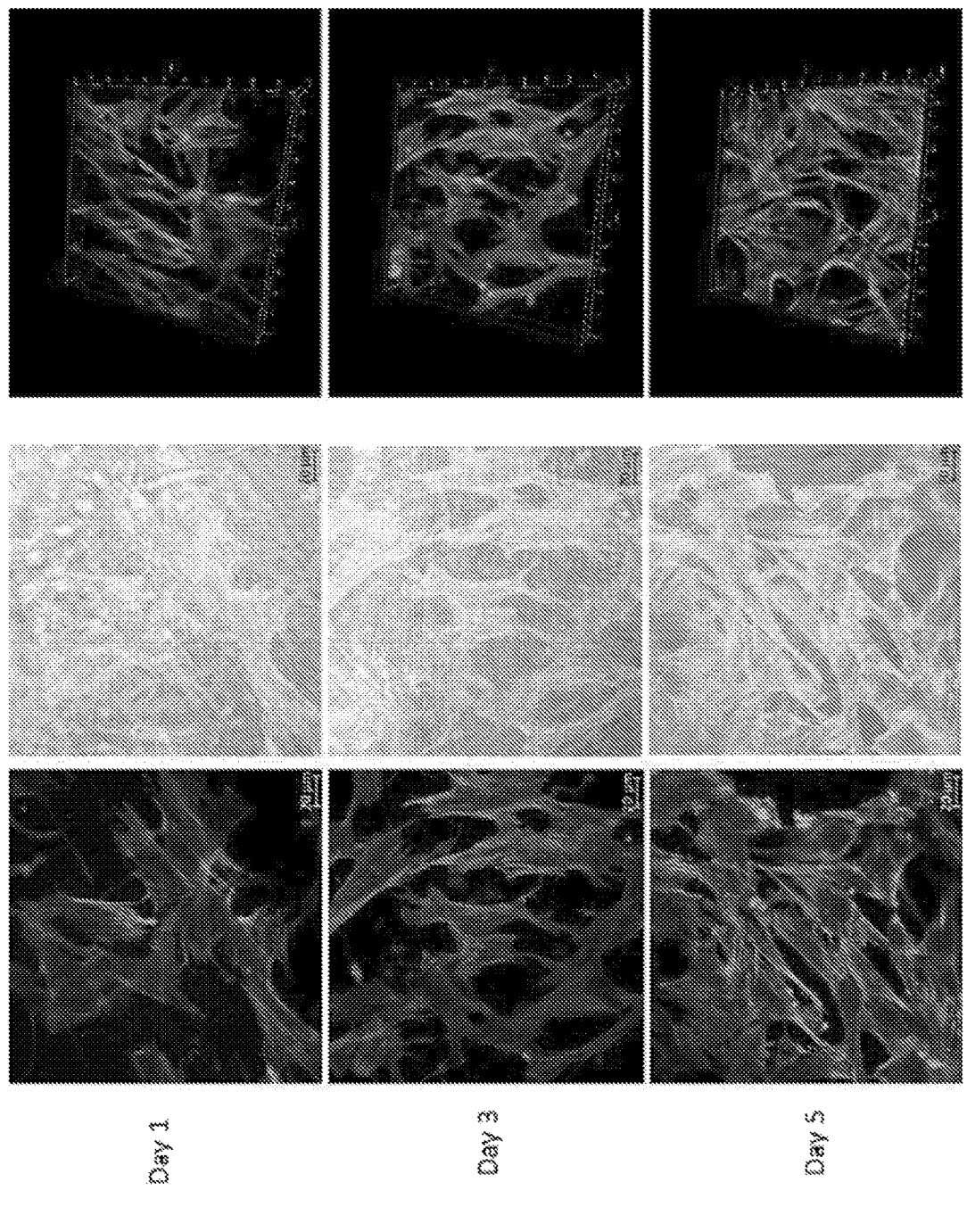
FIG. 9 shows representative fluorescence confocal microscopy images of human skin fibroblast cells.

FIG. 6A shows a fluorescence confocal microscopy image of human skin fibroblast cells bioprinted using peptide-based bioink (IVZK). FIG. 6B shows a fluorescence confocal microscopy 3D image of human skin fibroblast cells bioprinted using peptide-based bioink (IVZK). The progress over 14 days is illustrated in FIG. 9. In particular, FIG. 9 shows representative fluorescence confocal microscopy images of human skin fibroblast cells bioprinted using peptide-based bioink (IVZK) (left panel) and fluorescence confocal microscopy 3D images of human skin fibroblast cells bioprinted using peptide-based bioink (IVZK) (right panel). Cells were stained for F-actin (green) and nuclei (blue) for fluorescence microscopy studies. The printed structures using IVZK were cultured for 1, 3, 5, 7 and 14 days. Both 2D and 3D confocal microscopy images were taken at different locations on the same sample.

In further experiments, see FIG. 11A and FIG. 12A, immunostaining was performed after 1, 3, 7, 14 and 21 days of culture. Briefly, the cells were fixed with 3.7% paraformaldehyde solution for 30 minutes and incubated in a cold cytoskeleton buffer (3 mM $MgCl_2$, 300 mM sucrose and 0.5% Triton X-100 in PBS solution) for 10 minutes to permeabilize the cell membranes. The permeabilised cells were incubated in a blocking buffer for 30 minutes at 37° C. The blocking buffer solution contains 5% FBS, 0.1% Tween-20, and 0.02% sodium azide in PBS. In the next step, cells were incubated in an anti-vinculin (1:100) solution for one hour at 37° C. and further incubated in anti-mouse IgG (whole molecule)-FITC and rhodamine-phalloidin (1:200) for 1 hour at 37° C. Finally, the cells were incubated in DAPI for 10 minutes at 37° C. to counterstain the nucleus. The fluorescent dye-treated cells were imaged using a laser scanning confocal microscope (Zeiss LSM 710 Inverted Confocal Microscope, Germany). (Sundaramurthi et al., RSC Adv., 2015, 5, 69205-69214).

3D Cell Proliferation Assay

Figure 7:
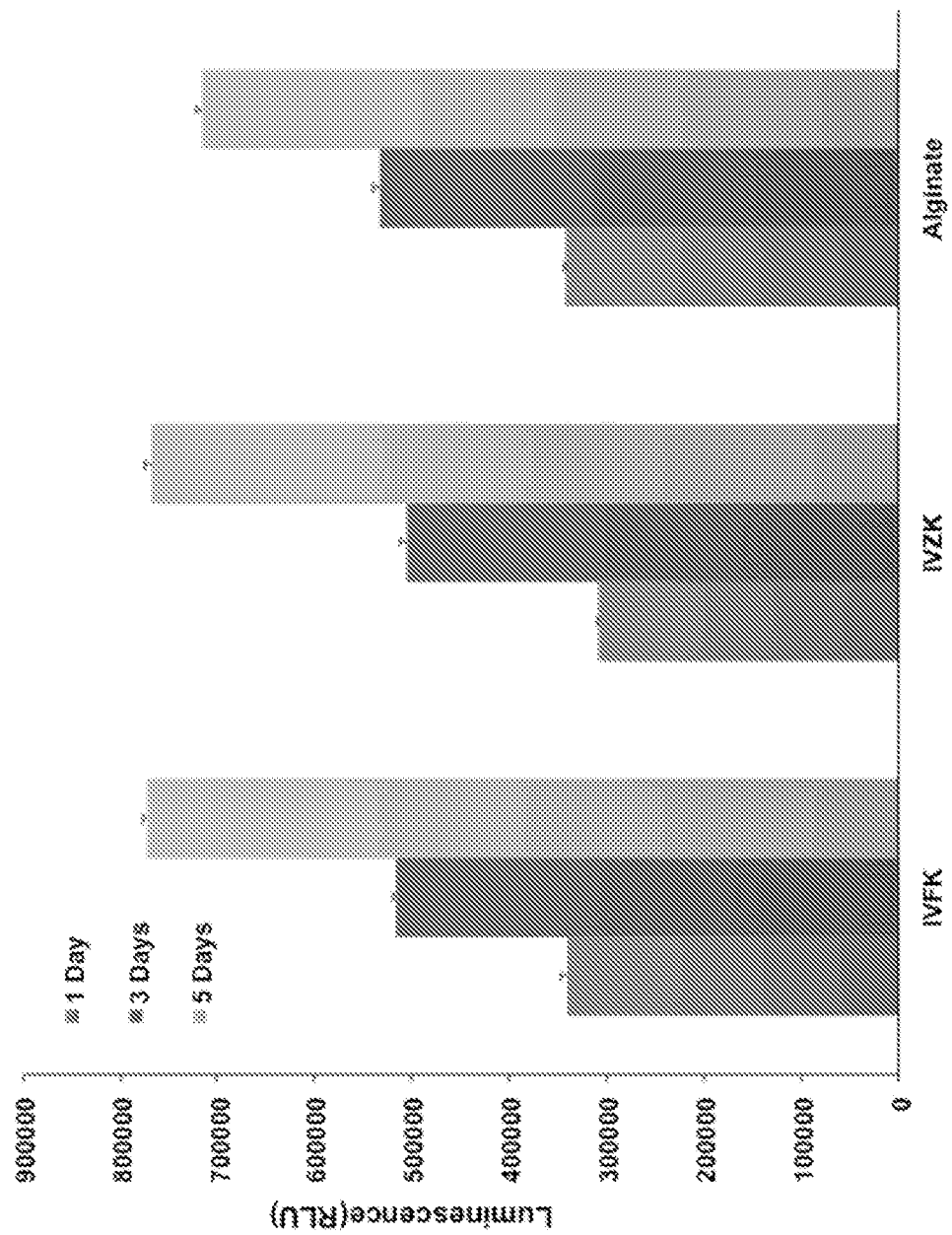
FIG. 7 is a cell viability assay as measured from ATP levels in 3D bioprinted human skin fibroblast cells using IVFK, IVZK peptides and alginate as bioinks.

FIG. 7 shows the cell viability assay as measured from ATP levels in 3D bioprinted human skin fibroblast cells using IVFK, IVZK peptides and alginate as bioinks.

The CellTiter-Glo® luminescent 3D cell viability assay was performed on 3D printed constructs containing human dermal fibroblast cells after different days (1, 3, 7 and 14) of culture. The quantification of the ATP using this method provides information about the metabolically active cells present in the construct. After each time point, the 3D constructs were washed twice with Dulbecco's phosphate-buffered saline (DPBS). Equal amounts of CellTiter-Glo® luminescent reagent and fresh cell culture medium were added to the samples. The contents were mixed for 2 minutes to digest the 3D hydrogel constructs and further incubated for 10 minutes. Finally, the luminescence was recorded using a plate reader (PHERAstar FS, Germany), see FIG. 7.

The CellTiter-Glo® luminescent 3D cell viability assay was also performed to determine the number of viable human bone marrow-derived mesenchymal stem cells (hBMSCs) in 3D hydrogels. After each time point, the hydrogels cultured with hBMSCs were washed twice with DPBS. Fresh medium was added to each well, and an equal amount of CellTiter-Glo® luminescent reagent was also added to the gels. The contents were mixed for 5 minutes to digest the hydrogels and then incubated for 30 minutes. After incubation, the luminescence was recorded using a plate reader (PHERAstar FS, Germany), see FIG. 12B.

Incorporation and In Situ Synthesis of Nanomaterials in the 3D Constructs

Figure 8:
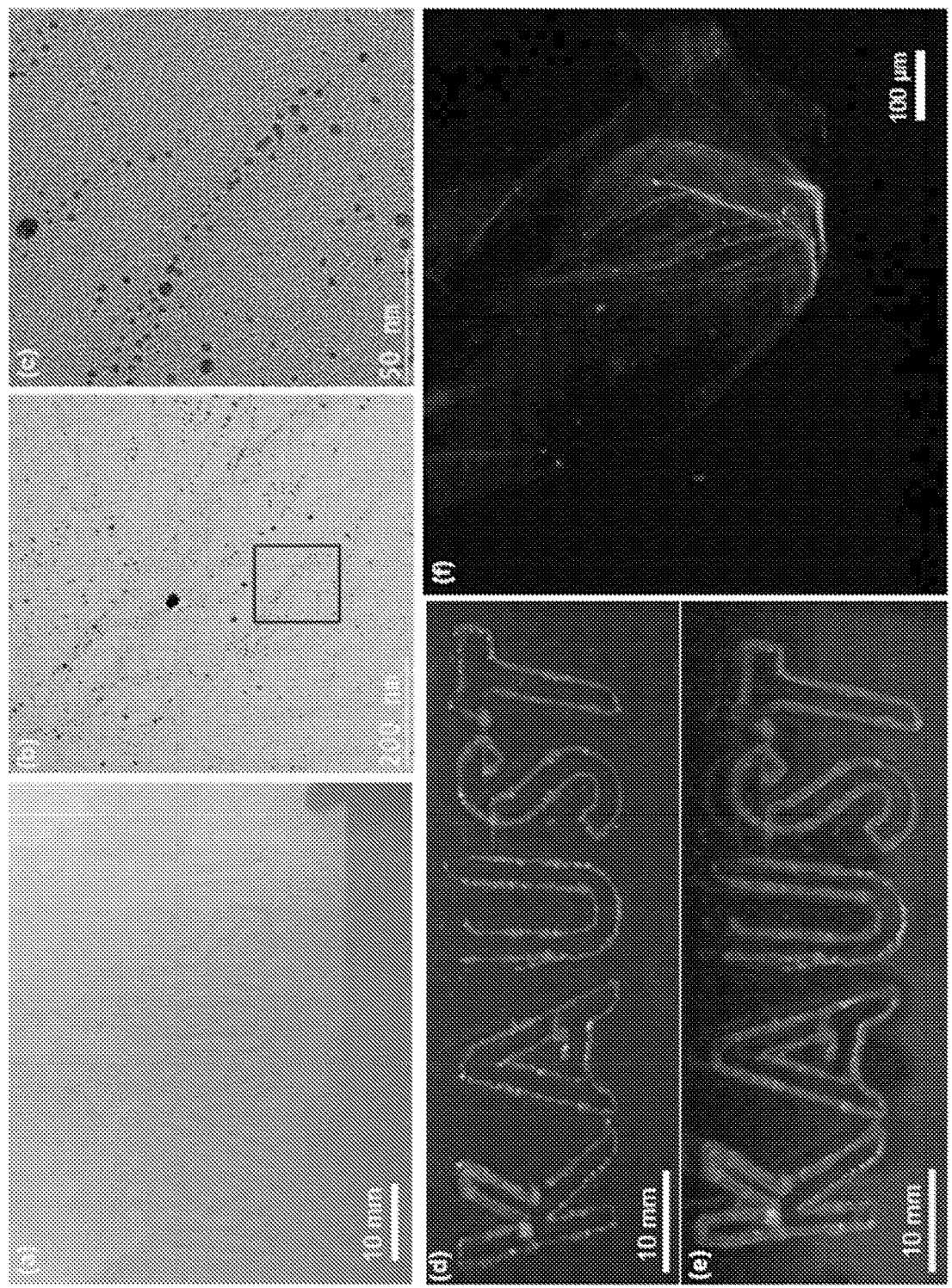
FIG. 8 In-situ synthesis and inclusion of nanomaterials in 3D bioprinted peptide hydrogels

We show the versatility of the 3D bioprinting method using tetramer peptides by printing nanomaterials within the peptide bioinks. FIG. 8A shows the in-situ synthesis of silver nanoparticles inside the 3D bioprinted construct. The peptide bioinks provided sufficient nucleation sites for silver ions, and after UV irradiation, silver nanoparticles were formed inside the 3D construct. The formation of silver nanoparticles appeared as yellowish color in the 3D bioprinted text (FIG. 8A) as compared to the transparent bioprinted text (FIG. 5, lower panel).

FIGS. 8B and 8C show transmission electron micrographs of silver nanoparticles prepared by in-situ synthesis of silver nanoparticles in the 3D printed structure of IVFK peptide bioinks. The 3D structure was printed using the IVFK peptide and silver nitrate (1 mM) mixture and subsequent illumination with UV light was used to produce silver nanoparticles.

FIG. 8F shows a fluorescence confocal microscopy image of green color quantum dots 3D printed with the peptide bioink (IVZK) showing that different nanomaterials can be incorporated into the printed structures, see also FIGS. 8D and 8E. This shows that peptide based bioinks can be used to perform in-situ synthesis of nanomaterials in 3D printed structures.

Different nanomaterials such as quantum dots and nanoparticles can be incorporated in the 3D peptide hydrogel using this printing method. As an example, streptavidin modified CdSe/ZnS quantum dots (QD 525, Invitrogen) were mixed with the peptide solution and 3D printed using the same procedure as described earlier. Fluorescence confocal microscopy (Zeiss LSM 710 Inverted Confocal Microscope, Germany) was used to confirm the presence of the quantum dots in the construct (FIG. 8F). The excitation wavelength for the quantum dots was 405 nm and emission wavelength maximum was 525 nm (green color). In another example, silver nanoparticles were generated in situ in the 3D peptide hydrogel construct by using the UV treatment (254 nm). The solution of silver nitrate ($AgNO_3$, 1 mM) was mixed with the peptide solution and after printing, UV light (254 nm for 10 min) was used to generate silver nanoparticles in the construct (FIGS. 8B and 8C). In this case, 100 mM Tris buffer (pH 8.5) was used instead of phosphate buffer saline (PBS).

Transmission Electron Microscopy (TEM) Studies

The TEM studies were carried out using FEI Titan G2 80-300 CT with a 300 kV emission gun. The TEM samples of 3D constructs containing in situ generated silver nanoparticles were prepared by transferring a small portion of the 3D construct on carbon coated copper grid using clean cotton swab. The grids were dried in normal air overnight before imaging (FIGS. 8B and 8C).

Figure 10:
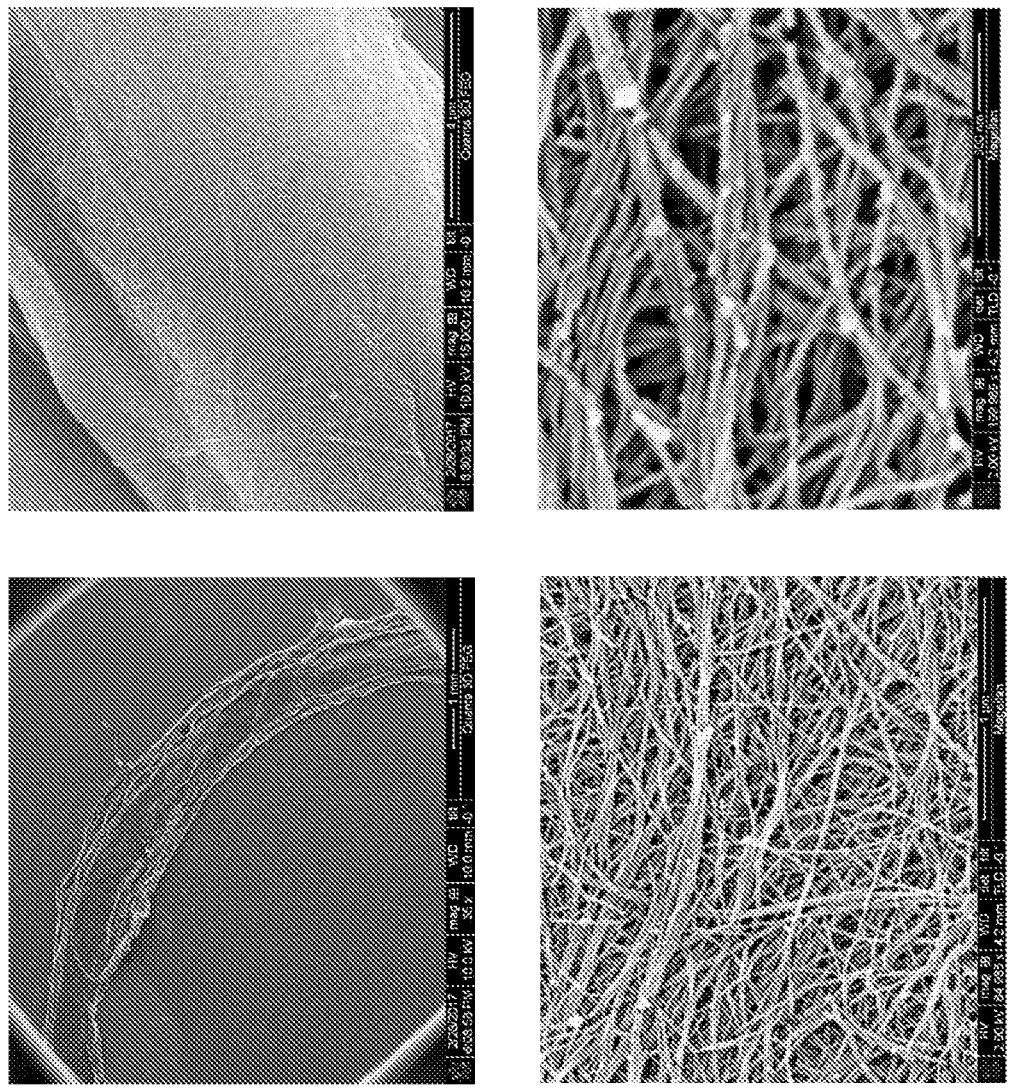
FIG. 10 shows scanning electron microscopy studies of 3D printed peptide hydrogel constructs.

FIG. 10 shows scanning electron microscopy studies of 3D printed peptide hydrogel constructs. For the low magnification images to show the circular ring (top), Quanta 3D FEG SEM/FIB microscope was used (10 kV). For high resolution images Magellan™ XHR SEM was used (2 kV).

In addition, human skin fibroblasts cells (HDFn) were 3D bioprinted into a simple ring structure in a layer-by-layer fashion with a diameter of about 8 mm and thickness of 1.2 mm. The 3D bioprinted constructs were cultured up to twenty-one days to test the biocompatibility of the peptide bioinks. As control, HDFn were 3D bioprinted in the same 3D circular shape using alginate-gelatin as bioink with a commercially available 3D bioprinter. Fluorescence confocal microscopy images showed the cytoskeletal staining of 3D bioprinted human skin fibroblasts (FIG. 11A). It can be seen that HDFn cells bioprinted with IVFK and IVZK attained excellent spreading after 21 days of culture as compared to alginate-gelatin as evident from the actin network (FIG. 11A). After 14 and 21 days of culture, the F-actin were well spread, stretched and distinct in IVZK while on IVFK they were dense but not well pronounced. After 14 and 21 days of culture, the F-actin expression was relatively low and less distinct in alginate-gelatin when compared to IVFK and IVZK.

Shape fidelity of the 3D bioprinted construct after cell culture is another critical parameter to access the quality of 3D bioprinted constructs. The ring structures printed with peptide bioinks maintained their shapes after 21 days of culture (FIG. 11B). Moreover, 3D cell viability assay (FIG. 11C) was performed to quantitatively evaluate the potential of bioprinted constructs to support the proliferation of HDFn cells in 3D. These results showed a time-dependent increase in cell proliferation in all the bioprinted constructs. The cell numbers were comparable between the IVZK, IVFK, and alginate-gelatin until seven days in culture (FIG. 11C). After 14 days and 21 days of culture, the cell proliferation in IVFK and IVZK were comparable but higher than that of alginate-gelatin. This shows that IVFK and IVZK provide native cues and offer more surface area to the cells to divide and grow due to their nanofibrous structure resemblance with the native ECM as compared to alginate-gelatin bioink. Also, these peptide hydrogels have sufficient porosity to accommodate more cells and maintain viability. On the contrary, alginate-gelatin does not possess nanofibrous architecture and also degrades faster in vitro.

Figure 12:
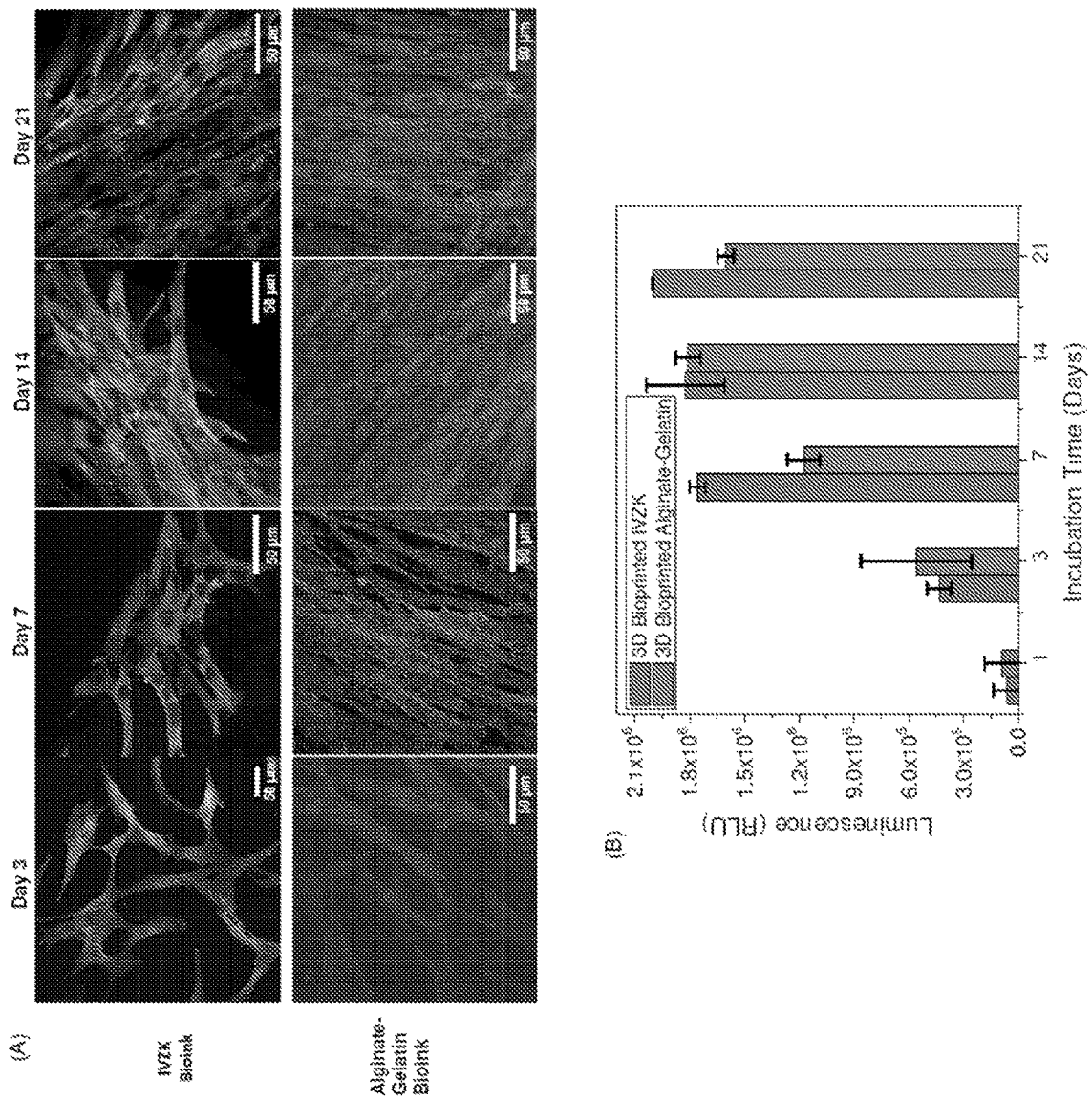

To show the versatile nature of our 3D bioprinting method and its potential to be used for other types of cells as well, we 3D bioprinted human bone marrow-derived mesenchymal stem cells (hBMSCs) using IVZK bioink and compared this with the alginate-gelatin bioink. Fluorescence confocal microscopy and 3D viability assay showed that peptide bioink allow better cell proliferation as compared to alginate-gelatin bioink (FIG. 12).

Peptide Spray

Two air spray brush nozzles were assembled in a casing made from Perspex sheet at an angle such that the stream from both the nozzles meet at one point (FIGS. 13A and B). One nozzle contained the peptide solution (5 mg/ml IVZK) and the second nozzle contained the phosphate buffer solution (10×). The peptide hydrogel was formed when both the streams intercepted each other on a silicon wafer surface. The sprayed peptide scaffolds were dried and finally imaged using scanning electron microscopy to study the fibrous network of the peptide hydrogel (FIG. 13C).

The airbrushes can be used with a device such as a robotic arm as shown in FIGS. 4A, 4B and 4C for direct spray of a peptide hydrogel onto a surface such as a wound site. The air brush assembly can also be used as a hand held device to directly spray the peptide hydrogels onto a surface such as a wound site.

The foregoing descriptions are only implementation manners of the present invention, the scope of the present invention is not limited to this. Any variations or replacements can be easily made through person skilled in the art. Therefore, the protection scope of the present invention should be subject to the protection scope of the attached claims.

The invention claimed is:

1. A device for printing a 3D object from a representation stored in a memory, the device comprising:
    a reservoir containing bioink solution;
    a first inlet configured to take in the bioink solution, which is a peptide solution,
    a second inlet configured to take in a buffer solution capable of inducing gelation of the bioink solution,
    a third inlet configured to take in a dispersion,
    a fluid duct for mixing the bioink solution, the buffer solution and the dispersion to obtain a peptide hydrogel, and
    a nozzle configured to eject a peptide hydrogel to build the 3D object,
    wherein the bioink solution comprises at least one peptide, having a general formula selected from:

$Z_o$—$X_nBX_mW$—$Z'_p$, and     a)

$Z_o$—$WX_mBX_n$—$Z'_p$,     b)

wherein Z is an N-terminal protecting group and Z' is a C-terminal protecting group, with o and p being independently selected from 0 and 1;
    wherein X is, independently at each occurrence, an aliphatic amino acid selected from isoleucine, norleucine, leucine, valine, alanine, glycine, homoallylglycine and homopropargylglycine with n and m being integers being independently selected from 0, 1 and 2, with the proviso that m+n≤2, wherein B is an aromatic amino acid selected from phenylalanine and tryptophan, or is an aliphatic counterpart of said aromatic amino acid, said aliphatic counterpart being selected from cyclohexylalanine; 4-hydroxy-cyclohexylalanine; and 3,4-dihydroxycyclohexylalanine, and wherein W is a polar amino acid selected from aspartic acid, glutamic acid, asparagine, glutamine, lysine, 5-N-ethyl-glutamine (theanine), citrulline, thiocitrulline, cysteine, homocysteine, methionine, ethionine, selenomethionine, telluromethionine, threonine, allothreonine, serine, homoserine, tyrosine, histidine, arginine, homoarginine, ornithine, lysine, N(6)-carboxymethyllysine, histidine, 2,4-diaminobutyric acid (Dab), 2,3-diaminopropionic acid (Dap), and N(6)-carboxymethyllysine.

2. The device of claim 1, wherein the fluid duct comprises a first region for mixing the bioink solution and the dispersion to obtain a bioink-dispersion mixture and a second region for mixing the bioink-dispersion mixture with the buffer solution.

3. The device of claim 1, wherein the dispersion comprises a cell culture medium, wherein the cell culture medium comprises a plurality of cell types.

4. The device of claim 1, wherein the dispersion comprises peptide nanoparticles, silver nanoparticles, gold nanoparticles, nanowires, quantum dots and/or carbon nanotubes.

5. The device of claim 4, wherein a plurality of cell types are encapsulated in the peptide nanoparticles and/or immobilized on a peptide nanoparticle surface.

6. The device of claim 1, further comprising a heating module configured to heat the fluid duct, and/or further comprising a micromixer.

7. The device of claim 1, further comprising one or more light emitters configured to irradiate the fluid duct.

8. The device of claim 7, wherein the light emitters comprise a first LED with a first wavelength and a second LED with a second wavelength different from the first wavelength.

* * * * *